United States Patent [19]

Norris et al.

[11] Patent Number: 5,246,844
[45] Date of Patent: Sep. 21, 1993

[54] VIRULENCE ASSOCIATED PROTEINS IN BORRELIA BURGDORFERI (BB)

[75] Inventors: Steven J. Norris, Houston; alan g. Barbour, San Antonio, both of Tex.

[73] Assignee: Board of Regents, The University of Texas System, Austin, Tex.

[21] Appl. No.: 781,355

[22] Filed: Oct. 22, 1991

[51] Int. Cl.⁵ .................... C12N 15/00; C12N 15/03; C12N 15/31
[52] U.S. Cl. ............... 435/172.3; 435/252.3; 435/252.33; 435/320.1; 536/23.7; 536/24.32; 536/24.33
[58] Field of Search ................ 536/27; 435/6; 424/92

[56] References Cited

U.S. PATENT DOCUMENTS

4,801,540  1/1989  Hiatt et al. .................. 435/240.4

OTHER PUBLICATIONS

Karlsson (J. Clin. Microbiol., 28(9):2148-2150, 1990).
Wallich et al. (Infect. Immun., 58(6):1711-1719, 1990).
Simpson et al. (J. Clin. Microbiol., 28(6):1329-1337, 1990).
Cluss and Boothby (Infect. Immun., 58(4):1038-1042, 1990).
Brandt et al. (Infect. Immun., 58(4):983-991, 1990).
Schutzer et al. (Lancet, 335:312-315, 1990).
Jiang et al. (J. Immunol., 144(1):284-289, 1990).
Borenstein et al. (Ann. Meet. Am. Soc. Microbiol., 90(0):46, Abstract #B-116, 1990).
Norris et al. (Ann. Meet. Am. Soc. Microbiol., 90(0):103, Abstract #D-135, 1990).
Luft et al. (Infect. Immun., 57(11):3637-3645, 1989).
Steere (New Engl. J. Med., 321(9):586-596, 1989).
Cunningham et al. (Ann. N.Y. Acad. Sci., 539:376-378, 1988).
Grodzicki and Steere (J. Infect. Dis., 157(4):790-797, 1988).
Barbour (Yale J. Biomed., 57:581-586, 1984).
Dialog Search Report.
Howe et al. "Organization of Genes Encoding Two Outer Membrane Proteins of (Lyme Disease Agent *Borrelia burgorferi* within a Single Transcriptional Unit" Inf. & Imm. 54(1) Oct. 1986, pp. 207-212.

*Primary Examiner*—Christine M. Nucker
*Assistant Examiner*—Chris Dubrule
*Attorney, Agent, or Firm*—Arnold, White & Durkee

[57] ABSTRACT

The invention relates to a DNA segment encoding a *Borrelia burgdorferi* antigenic polypeptide. The invention also relates to a purified 30 kDa polypeptide isolated from a virulent strain of *B. burgdorferi* and to epitopic segments of the polypeptide with immunogenic potential. The 30 kDa protein provides a route for the development of immunodiagnostics for Lyme disease and related disorders. The 30 kDa protein and related amino acid and DNA sequences may also be used for the immunization, for the detection of *B. burgdorferi* in human or animal tissues or body fluids, and also for the generation of specific antibodies for use in diagnosis, epidemiology, and prevention of Lyme disease.

22 Claims, 14 Drawing Sheets

```
         -300                -280                -260
          .                   .                   .
AAGCTTGCATGCTATATAATAGCTTTTCACATAGTTTATAGATAACACCGCAAATTAAAG

-240                -220                -200
          .                   .                   .
ACAATTCTCTATAAAAGTTAATTTTTTTNNCTTGTTTTAGCATCATTAAACATCCTTTC

-180                -160                -140
          .                   .                   .
AATACTCACTATTGTTTTCTTAGCCTTAAGCTAGCCAAGCTAAATAGAAATTAGTAGGCA

-120                -100                -80
          .                   .                   .
ATTGATATTAAAATATAATTGATATTAAAATATAATTGATATTAAAATATAATTGATATT

-60                 -40                 -20
          .                   .                   .
AAAATATAATTGATATTAAAATATAATTGATATTGAAATATAATTGATATTAAAATATAA 0                   20                  40
          .                   .                   .
TTTAAGACATTATATTTAAGGAGTATAAATATGAAAAAATTAATAAAATACTACTGTTA
                                M  K  K  L  I  K  I  L  L  L
```

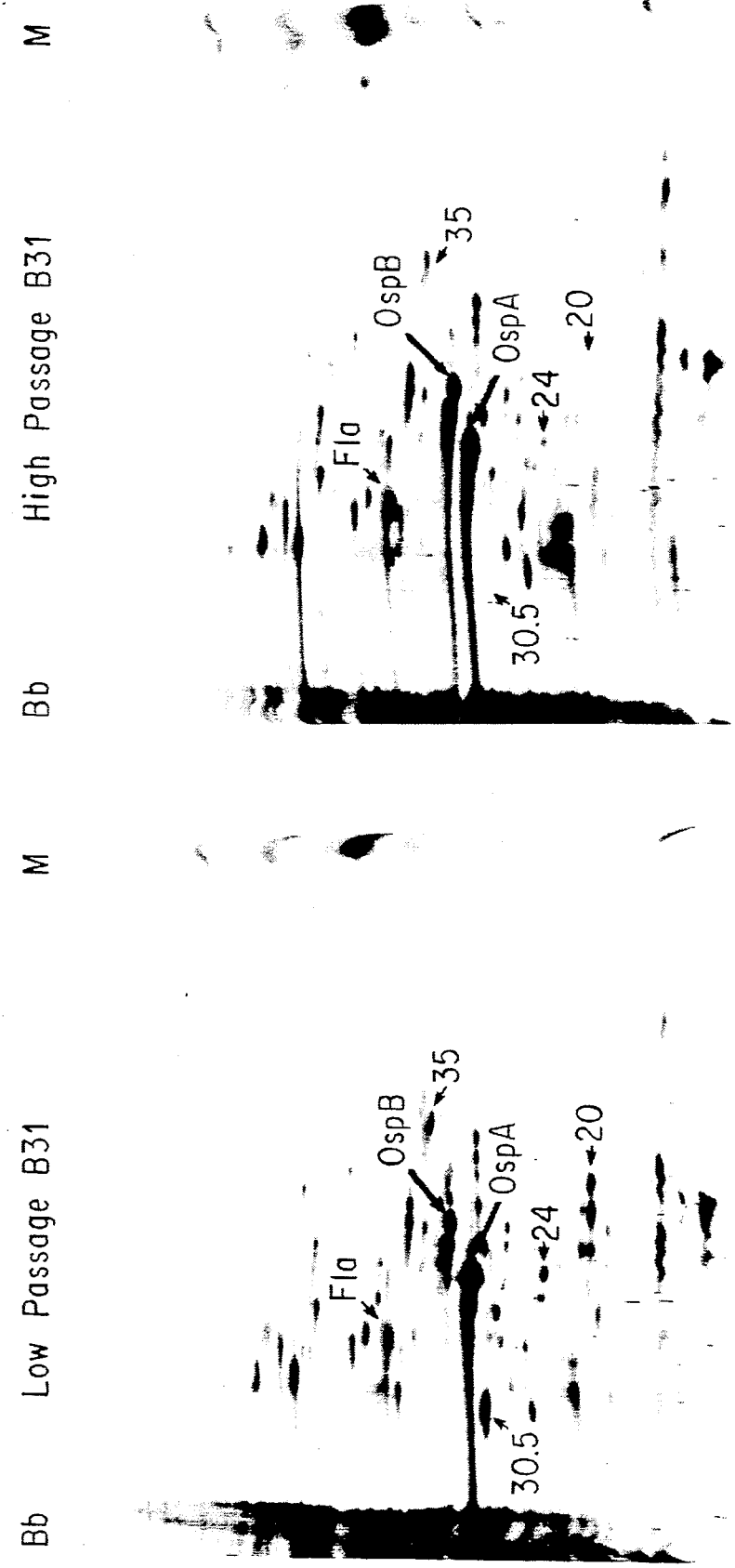

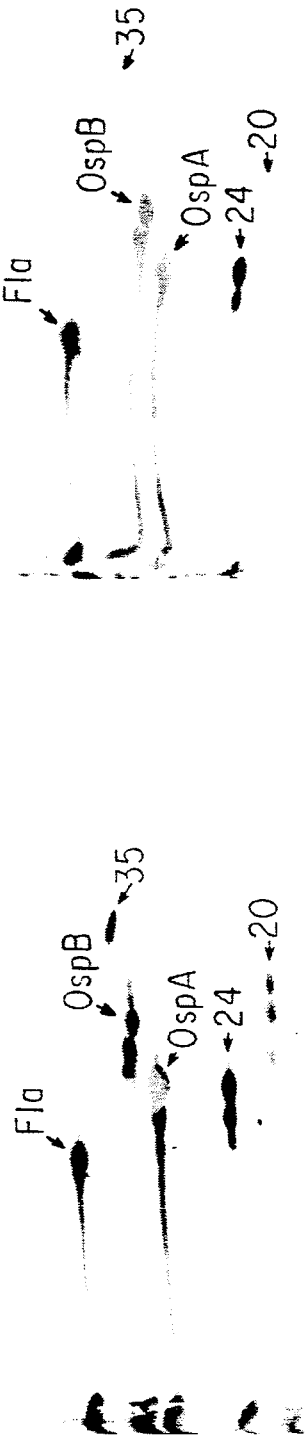

```
 10
MetLysLysLeuIleLysIleLeuLeuPheLeuLeuLeuSerIleSerCys

30
ValHisAspLysGlnGluLeuSerSerLysSerAsnLeuAsnAsnGlnLysGlyTyrLeu

50
AspAsnGluGlyAlaAlaAsnSerAsnTyrGluSerLysLysGlnSerIleLeuSerGluLeu

70
AsnGlnLeuLeuLysGlnThrThrThrAsnSerLeuLysGluAlaLeuLysAsnThrThrAspAsn

90
LeuAsnAlaSerAsnGluAlaAlaAsnLysValValGluAlaAlaAsnAlaValIleAsnAlaValAsnLeu

110
IleSerSerAlaAlaAspGlnValLysSerAlaThrLysAsnMetHisAspLeuAlaGln

130
MetAlaGluIleAspLeuGluLysIleLysAsnSerSerAspLysAlaIlePheAlaSer
```

FIG. 3A

```
                    150
AsnLeuAlaAlaTyrSerLeuThrLysAlaAlaAlaGluGlnAsnMetGlnLysLeu
                    170
TyrLysGluGlnGlnLysIleSerGluSerGluSerAspTyrSerAspSerAla
                    190
GluIleLysGlnAlaLysGluAlaValGluIleAlaAlaTrpLysAlaThrValGluAlaLys
                    210
AspLysLeuIleAspValGluAsnThrValLysGluThrLeuAspLysIleLysThrGlu
                    230
ThrThrAsnAsnThrLysLeuAlaAspIleLysGluAlaAlaGluLeuValAlaLeuAsnThr
                    250
AlaLysAsnAlaLysGluIleValGlnGluValValAlaAlaLeuLeuAsnThr
```

FIG. 3B

```
-300                        -280                        -260
AAGCTTGCATGCTATATAATAGCTTTTCACATAGTTTATAGATAACACCGCAAATTAAAG

-240                        -220                        -200
ACAATTCTCTATAAAAGTTAATTTTTTTNNCTTGTTTTTAGCATCATTAAACATCCTTTC

-180                        -160                        -140
AATACTCACTATTGTTTTCTTAGCCTTAAGCTAGCCAAGCTAAATAGAAATTAGTAGGCA

-120                        -100                         -80
ATTGATATTAAAATATAATTGATATTAAAATATAATTGATATTAAAATATAATTGATATT

-60                         -40                         -20
AAAATATAATTGATATTAAAATATAATTGAAATATATTAAAATATAA 0                           20                          40
TTTAAGACATTATATATTTAAGGAGTATAAATATGAAAAAATTAATAAAATACTACTGTTA
                              M  K  K  L  I  K  I  L  L  L
```

FIG. 5A

```
        60                    80                   100
AGTTTATTTTATTGCTCTCTCAATATCTTGTGTTCATGATAAACAAGAATTATCATCAAAA
 S  L  F  L  L  L  S  I  S  C  V  H  D  K  Q  E  L  S  S  K 120                   140                   160
TCTAATTTAAATAATCAAAAGGATATTTAGATAATGAAGGCGCAAATTCAAATTACGAA
 S  N  L  N  N  Q  K  G  Y  L  D  N  E  G  A  N  S  N  Y  E 180                   200                   220
TCAAAAAACAGAGCATATTAAGTGAGTTAAATCAGTTATTAAAGCAAACTACAAATTCA
 S  K  K  Q  S  I  L  S  E  L  N  Q  L  L  K  Q  T  T  N  S 240                   260                   280
CTAAAGAAGCCAAAAATACAACAGATAATTTAAATGCATCAAATGAGGCAAATAAAGTT
 L  K  E  A  K  N  T  T  D  N  L  N  A  S  N  E  A  N  K  V
```

FIG. 5B

```
                                                      300                              320                              340
                                                       .                                .                                .
                                              GTAGAAGCGGTTATAAATGCAGTTAATTTAATTTCATCTGCTGCAGATCAAGTAAAAGT
                                               V  E  A  V  I  N  A  V  N  L  I  S  S  A  A  D  Q  V  K  S 360                              380                              400
                                                       .                                .                                .
                                              GCAACAAAAAATATGCATGATTTAGCTCAAATGGCAGAAATAGATTTAGAAAAATAAAG
                                               A  T  K  N  M  H  D  L  A  Q  M  A  E  I  D  L  E  K  I  K 420                              440                              460
                                                       .                                .                                .
                                              AACTCTAGTGATAAAGCAATATTTGCATCTAATCTTGCAAAAGAAGCATATAGCCTTACT
                                               N  S  S  D  K  A  I  F  A  S  N  L  A  K  E  A  Y  S  L  T 480                              500                              520
                                                       .                                .                                .
                                              AAAGCAGCAGAAACAAATGCAAAAACTGTATAAAGAGCAACAAAAATATCAGAATCA
                                               K  A  A  E  Q  N  M  Q  K  L  Y  K  E  Q  Q  K  I  S  E  S 540                              560                              580
                                                       .                                .                                .
                                              GAATCAGAATCTGACTATTCTGATTCTGCTGAAATAAAACAAGCTAAAGAGGCCGTAGAA
                                               E  S  E  S  D  Y  S  D  S  A  E  I  K  Q  A  K  E  A  V  E
```

FIG. 5C

```
                                    600                              620                              640
                                     .                                .                                .
ATAGCTTGGAAAGCTACAGTAGAAGCAAAAGATAAGTTAATTGATGTAGAAAATACAGTC
 I  A  W  K  A  T  V  E  A  K  D  K  L  I  D  V  E  N  T  V 660                              680                              700
                                     .                                .                                .
AAAGAGACATTGGATAAAATAAAGACAGAAACTACGAACAATACAAAGCTT
 K  E  T  L  D  K  I  K  T  E  T  T  N  N  T  K  L
```

FIG. 5D

VIRULENCE ASSOCIATED PROTEINS IN *BORRELIA BURGDORFERI* (BB)

The United States Government may have certain rights in the present invention pursuant to Grant No. AI 24424 and Grant No. AI 29731 awarded by the National Institutes of Health.

BACKGROUND OF THE INVENTION

1. Field of the Invention

The present invention relates to nucleic acid sequences encoding antigenic proteins associated with *Borrelia burgdorferi* (Bb), particularly polypeptides associated with virulence. The invention also relates to methods for producing *Bb* immunogenic polypeptides and corresponding antibodies. Other embodiments of the invention relate to methods for detecting Lyme disease and transformed cells comprising *Bb*-associated nucleic acids.

2. Description of Related Art

Lyme disease is a multisystem disease resulting from tick transmission of the infectious agent, *Borrelia burgdorferi* (*Bb*) (Rahn and Malawista, 1991). Although recognized as a clinical entity within the last few decades (Steere et al., 1977), case reports resembling Lyme disease date back to the early part of the 20th century. Cases of the disease have been reported in Europe, Asia and North America (Schmid, 1985). Despite a relatively low total incidence compared to other infectious diseases, Lyme disease represents a significant health problem because of its potentially severe cardiovascular, neurologic and arthritic complications, difficulty in diagnosis and treatment and high prevalence in some geographic regions.

There is increasing evidence that Bb is not a homogeneous group but has a variable genetic content, which may in turn affect its virulence, pattern of pathogenesis and immunogenicity. Its virulence factors, pathogenetic mechanisms and means of immune evasion are unknown. At the level of patient care, diagnosis of the disease is complicated by its varied clinical presentation and the lack of practical, standardized diagnostic tests of high sensitivity and specificity. Antimicrobial therapy is not always effective, particularly in the later stages of the disease.

Variation among *Bb* strains and the changes resulting from in vitro passage add to the problems of developing vaccines or immunodiagnostics from either the whole organism or specifically associated proteins. Using a PCR assay, it was found that one set of oligonucleotide primers was specific for North American *Bb* isolates, another for most European isolates and a third set recognized all *Bb* strains (Rosa et al., 1989).

Serological assays for the diagnosis and detection of Lyme disease are thought to offer the most promise for sensitive and specific diagnosis. However, serologic assays generally use whole *Bb* as antigen and suffer from a low "signal to noise" ratio, i.e., a low degree of reactivity in positive samples, particularly early in the disease, as compared to negative samples. This problem results in high numbers of false negatives and the potential for false positives. Background reactivity in negative controls may be due in part to conserved antigens such as the 41K flagellin and the 60K "Common Antigen". These *Bb* proteins possess a high degree of sequence homology with similar proteins found in other bacteria. Therefore normal individuals will often express anti-flagellar and anti-60K antibodies. Unique, highly reactive *Bb* antigens for serological assays are therefore desirable but heretofore unavailable.

Diagnosis of Lyme disease remains a complex and uncertain endeavor, due to lack of any single diagnostic tool that is both sensitive and specific. Clinical manifestations and history are the most common bases for diagnosis. However, there is a pressing need for specific, sensitive, reproducible and readily available confirmatory tests. Direct detection offers proof of infection but is hampered by the extremely low levels of *Bb* that are typically present during infection, as well as the inaccessibility of sites that tend to be consistently positive (e.g., heart and bladder). Culture, although sensitive, is cumbersome and requires 1-3 weeks to obtain a positive result. PCR appears to offer promise in terms of direct detection (Lebech et al., 1991) and indeed Goodman et al (1991) have reported detection of *Bb* DNA in the urine of patients with active Lyme disease using a PCR method. However, it is unlikely that PCR assays will become commonly used in clinical laboratories because of the degree of skill required for its use and the high risk of DNA contamination.

Another problem in detection of Lyme disease is the substantial number of humans exposed to *Bb* who develop inapparent or asymptomatic infections. This number has been estimated as high as 50% (Steere et al., 1986).

There is clearly a need for means of preparing *Bb*-specific antigens, e.g., for the development of diagnostic tests for Lyme disease. Adequate assays do not exist and should ideally meet several criteria, including (1) expression of an antigen by all pathogenic *Bb* strains, (2) elicitation of an immune response in all Lyme disease patients, (3) high immunogenicity with a detectable antibody response early in the infection stage, (4) antigens unique to *Bb* without cross reactivity to other antigens and, (5) distinction between individuals exposed to nonpathogenic as opposed to pathogenic forms of *Bb*.

SUMMARY OF THE INVENTION

The present invention addresses one or more of the foregoing or other problems associated with the preparation and use of *Bb*-specific antigens, particularly those antigens associated with virulence and which are useful for developing detection and diagnostic methods for Lyme disease. The invention involves the identification of such antigens, as well as the identification and isolation of *Bb* nucleic acid sequences that encode *Bb* antigens or antigenic polypeptides derived therefrom. These sequences are useful for preparing expression vectors for transforming host cells to produce recombinant antigenic polypeptides. It is further proposed that these antigens will be useful as vaccines or immunodiagnostic agents for *B. burgdorferi* associated diseases such as Lyme disease in particular.

The nucleic acid segments of the present invention encode antigenic amino acid sequences associated with virulent *Bb*. These sequences are important for their ability to selectively hybridize with complementary stretches of *Bb* gene segments. Varying conditions of hybridization may be desired, depending on the application envisioned and the selectivity of the probe toward the target sequence. Where a high degree of selectivity is desired, one may employ relatively stringent conditions to form the hybrids, such as relatively low salt and/or high temperature conditions. Under these conditions, little mismatch between the probe and template or target strand is tolerated. Less stringent conditions might be employed where, for example, one desires to prepare mutants or to detect mutants when significant divergence exists.

In clinical diagnostic embodiments, nucleic acid segments of the present invention may be used in combination with an appropriate means, such as a label, to determine hybridization with DNA of a pathogenic organism. Typical methods of detection might utilize, for example, radioactive species, enzyme-active or other marker ligands such as avidin/biotin, which are detectable directly or indirectly. In preferred diagnostic embodiments, one will likely desire to employ an enzyme tag such as alkaline phosphatase or peroxidase rather than radioactive or other reagents that may have undesirable environmental effects. Enzyme tags, for example, often utilize colorimetric indicator substrates that are readily detectable spectrophotometrically, many in the visible wavelength range. Luminescent substrates could also be used for increased sensitivity.

Hybridizable DNA segments may include any of a number of segments of the disclosed DNA. For example, relatively short segments including 12 or so base pairs may be employed, or, more preferably when probes are desired, longer segments including 20, 30 or 40 base pairs, depending on the particular applications desired. Shorter segments are preferred as primers in such applications as PCR, while some of the longer segments are generally preferable for blot hybridizations. It should be pointed out, however, that while sequences disclosed for the DNA segments of the present invention are defined by SEQ ID NO: 1, e.g., segments 152 to 188, a certain amount of variation or base substitution would be expected, e.g., as may be found in mutants or strain variants, but which do not significantly affect hybridization characteristics. Such variations, including base modifications occurring naturally or otherwise, are intended to be included within the scope of the present invention.

In embodiments relating to antigen production, DNA segments are disclosed that encode an antigenic polypeptide derived from the amino acid sequence of an antigen of *Bb*. Particularly preferred for such an application is the 30 kDa *Bb* antigen. However, it is proposed that various other *Bb*-specific antigens have been identified and may be obtained employing the procedures disclosed herein, including, e.g., the 35 kDa, 24 kDa, and 20 kDa antigens. Until now, antigenic proteins appearing to be uniquely associated with virulence, such as the 30 kDa species, have not been isolated, purified or characterized. Through the present invention, recombinant means to obtain e.g., the 30 kDa protein and its epitopes in useful amounts have been provided. It is particularly noteworthy that the invention provides for the identification and selection of antigens such as the 30 kDa antigen that are associated with low passage, virulent *Bb* strains so that a selective detection method for virulent strains of *Bb* is now possible.

While the 30 kDa *Bb* antigen has been disclosed in terms of a specific amino acid sequence, it is nonetheless contemplated that the amino acid sequence will be found to vary from isolate to isolate. Moreover, it is quite clear that changes may be made in the underlying amino acid sequence through e.g., site-directed mutagenesis of the DNA coding sequence, in a way that will not negate its antigenic capability.

The invention also relates to at least partially purified antigenic *Bb* proteins or polypeptides which are capable of producing an in vivo immunogenic response when challenged with *Bb*. These proteins may comprise all or part of the amino acid sequence encoded by the herein disclosed DNA. A particularly preferred antigenic protein has the amino acid sequence shown in FIG. 3, SEQ ID NO: 2. This protein, as well as its epitopes, will be useful in connection with vaccine development, and as antigen(s) in immunoassays for detection of *Bb* antibodies in biological fluids such as serum, seminal or vaginal fluids, urine, saliva, body exudates and the like.

In other aspects, the invention concerns recombinant vectors such as plasmids, phage or viruses, which comprise DNA segments in accordance with the invention, for use in replicating such sequences or even for the expression of encoded antigenic peptides or proteins. Vectors or plasmids may be used to transform a selected host cell. In preparing a suitable vector for transforming a cell, desired DNA segments from any of several *Bb* sources may be used, including genomic fragments, cDNA or synthetic DNA. In practice of the present invention, an expression vector may incorporate at least part of the DNA sequence of SEQ ID NO: 1, encoding one or more epitopic segments of the disclosed 30 kDa antigen.

Expression vectors may be constructed to include any of the DNA segments hereinabove disclosed. Such DNA might encode an antigenic protein specific for virulent strains of *Bb* or even hybridization probes for detecting *Bb* nucleic acids in samples. Longer or shorter DNA segments could be used, depending on the antigenic protein desired. Epitopic regions of the 30 kDa protein expressed or encoded by the disclosed DNA could be included as relatively short segments of DNA. A wide variety of expression vectors is possible including, for example, DNA segments encoding reporter gene products useful for identification of heterologous gene products and/or resistance genes such as antibiotic resistance genes which may be useful in identifying transformed cell.

Recombinant vectors such as those described are particularly preferred for transforming bacterial host cells. Accordingly, a method is disclosed for preparing transformed bacterial host cells that includes generally the steps of selecting a suitable bacterial host cell, preparing a vector containing a desired DNA segment and transforming the selected bacterial host cell. Several types of bacterial host cells may be employed, including *Bb*, *E. coli*, *B. subtilus*, and the like as well as prokaryotic host cells.

Transformed cells may be selected using various techniques, including screening by differential hybridization, identification of fused reporter gene products, resistance markers, anti-antigen antibodies and the like. After identification of an appropriate clone, it may be selected and cultivated under conditions appropriate to the circumstances, as for example, conditions favoring expression or, when DNA is desired, replication conditions.

Another aspect of the invention involves the preparation of antibodies and vaccines from the antigenic 30 kDa protein or epitopic regions of that protein encoded by the disclosed DNA. The invention thus relates to one or more antibodies, monoclonal or polyclonal, that may be generated in response to the 30 kDa *Bb* protein or its epitopes. It is expected that the sensitivity and specificity of antibody response to this 30 kDa protein and its epitopes will be superior to the response that has been obtained from other *Bb* antigens that are not associated with virulence. Previous work with several *Bb* antigens isolated from both virulent and avirulent strains indicated low sensitivity when immunofluorescence and ELISA assays were employed, especially during early stages of infection.

In both immunodiagnostics and vaccine preparation, it is often possible and indeed more practical to prepare antigens from segments of a known immunogenic protein or polypeptide. Certain epitopic regions may be used to produce responses similar to those produced by the entire antigenic polypeptide. Potential antigenic or immunogenic regions may be identified by any of a number of approaches, e.g., Jameson-Wolf or Kyte-Doolittle antigenicity analyses or Hopp and Woods (1981) hydrophobicity analysis (see, e.g., Kyte and Doolittle, 1982, or U.S. Pat. No. 4,554,101). Hydrophobicity analysis assigns average hydrophilicity values to each amino acid residue from these values average hydrophilicities can be calculated and regions of greatest hydrophilicity determined. Using one or more of these methods, regions of predicted antigenicity may be derived from the amino acid sequence assigned to, e.g., the 30 kDa polypeptide. Proposed epitopic regions from the 30 kDa antigen include the sequences corresponding to positions 64–87, 106–114, 23–54, 128–133, 152–188 and 208–226.

It is contemplated that the antigens and immunogens of the invention will be useful in providing the basis for one or more assays to detect antibodies against *Bb*. Previous assays have used whole *Bb* as the antigen. Sera from normal individuals not exposed to *Bb* often contain antibodies that react with *Bb* antigens, in particular antigens that have epitopes in common with other bacteria. It is necessary to adjust assay conditions or the diagnostic threshold of reactivity to avoid false positive reactions due to these cross-reactive antibodies in normal sera. These adjustments may in turn decrease the sensitivity of the assay and lead to false negative reactions, particularly in the early stages of *Bb* infection. Assays using the disclosed 30 kDa protein or antigenic polypeptides thereof, are expected to give superior results both in sensitivity and selectivity when compared to assays that use whole *Bb* or even purified flagella in either an indirect ELISA or an antibody capture ELISA format. Western immunoblots based on reactions with such antigens (whole *Bb*, flagella and the like) have been difficult to interpret due to the presence of antibodies in sera from unexposed individuals. These antibodies cross react with *Bb* antigens, most particularly the 41 kDa flagellin and the 60 kDa common antigen protein. Generally, assays which us whole organisms or purified flagella tend to contain antigens with epitopes that will cross react with other bacterial antigens. For example, the N and C terminal regions of the *Bb* flagellin possess 52–55% sequence identity with the *Salmonella typhimurium* and *Bacillus subtilis* sequences (Wallich et al., 1990), exemplifying the highly conserved nature of flagellin structure. The 60 kDa Bb protein is likewise 58% homologous with the *E. coli* protein (Shanafelt et al., 1991). Such cross reactivity is not likely with the 30 kDa antigen, which is apparently unique to *Bb*.

It is further anticipated that a recombinant derived 30 kDa *Bb* protein will be particularly preferred for detecting *Bb* infections. Unexposed individuals should have a low reactivity to one or more epitopes of the 30 kDa protein thereby making it possible to use lower dilutions of serum and increase sensitivity. Using a combination of more than one of these unique antigens may also enhance sensitivity without sacrificing specificity.

Preferred immunoassays are contemplated as including various types of enzyme linked immunoassays (ELISAS), immunoblot techniques, and the like, known in the art. However, it will be readily appreciated that utility is not limited to such assays, and useful embodiments include RIAs and other nonenzyme linked antibody binding assays or procedures.

Yet another aspect of the invention is a method of detecting *Bb* nucleic acid in a sample. The presence of *Bb* nucleic acid in the sample may be indicated by the presence of the polypeptide products which it encodes. The method therefore includes detecting the presence of at least a portion of any of the polypeptides herein disclosed. Suitable detection methods include, for example, immunodetection reagents, PCR amplification, and hybridization.

Yet another aspect of the invention includes one or more primers capable of priming amplification of the disclosed DNA of SEQ ID NO: 1. Such primers are readily generated taking into account the base sequence of the DNA segment of SEQ ID NO:2, the disclosed DNA, or deriving a base sequence from the amino acid sequence of a purified polypeptide encoded by the DNA. Primers are analogous to hybridization probes, but are generally relatively short DNA segments, usually about 7–20 nucleotides.

Methods of diagnosing Lyme disease are also included in the invention. In one embodiment, an antibody-based method includes obtaining a sample from a patient suspected of having Lyme disease, exposing that sample to one or more epitopes of the *Bb* protein which is encoded by the DNA disclosed and finally determining a reactivity of the antibody with one or more epitopes of a *Bb* protein that may be in the sample. The reactivity measured is indicative of the presence of Lyme disease. Typical samples obtainable from a patient include human serum, plasma, whole blood, cerebrospinal fluid, seminal or vaginal fluids, exudates and the like.

Several variations of antibody-based methods are contemplated for development; for example, an indirect ELISA using the 30K protein or other *Bb* proteins as an antigen. The 30K protein may be produced in large quantities by recombinant DNA vectors already disclosed and purified. Optimal concentration of the antigen could be determined by checker board titration and diagnostic potential of the 30 kDa protein assay examined further by testing serum from mice at different stages of infection and infected with different strains of *Bb*. These results could indicate the relative time course for sera conversion for each of the assays and would also show whether infection with different strains causes variation in anti-30 kDa protein titers.

Likewise, reactive epitopes of the 30 kDa polypeptide are contemplated as useful either as antigens in an ELISA assay or to inhibit the reaction of antibodies toward intact 30 kDa protein bound to a well. Epitopic peptides could be generated by recombinant DNA techniques previously disclosed or by synthesis of peptides from individual amino acids. In either case, reaction with a given peptide would indicate presence of antibodies directed against more epitopes. In addition to its diagnostic potential, this method is seen as being particularly effective in characterizing monoclonal antibodies against the 30 kDa protein and other virulence associated proteins.

The invention also relates to monoclonal antibodies directed toward one or more epitopes of the antigenic protein encoded by the disclosed DNA. In preferred embodiments, such antibodies lack cross reactivity with antigens found in other bacteria. Monoclonal antibodies against the 30 kDa protein and other virulence associated proteins are generated by using hybridomas which can be produced and screened. Proteins produced by Bb or recombinant DNA vectors and purified by two-dimensional electrophoresis or other methods could be used for immunization of animal models such as BALB/C mice. Selection of reactive clones is carried out with a typical ELISA assay using the immunizing protein as antigen. Western immunoblots could also be used in a screening or confirmatory assay.

Such monoclonals are envisioned as useful in several respects including (1) detection of Bb in tissues or body fluids by immunofluorescence, enzyme immunoreactions, such as immunoperoxidase staining of tissue sections, avidin-biotin indicator enzyme immunoassays, or other techniques, (2) rapid screening of Bb strains and clones as well as E. coli recombinants for expression of the protein, (3) determination of structural locations of proteins by immuno electron microscopy, (4) identification of reactive epitopes using a peptide library, (5) demonstration of bacteriocidal activity in vitro in combination with compliment and selection of protein deficient mutants, (6) assessment of immunoprotective activity by passive immunization, (7) use to study host cell interactions by inhibition of adherence or penetration or by enhancement or engulfment and killing by phagocytic cells, and (8) possible use for epidemiological studies particularly in studying variation of Bb strains in expression of proteins or protein sequences.

In further aspects, the present invention concerns a kit for the detection of Bb antigens, the kit including, alternatively, an antibody reactive with antigenic protein 30 kDa or a protein or peptide which includes an epitope thereof, together with means for detecting a specific immunoreaction between an antibody ad its corresponding antigen. Examples of suitable means include labels attached directly to the antigen or antibody, a secondary antibody having specificity for human Ig, or protein A or protein G. Alternatively, avidin-biotin mediated Staphylococcus aureus binding could be used. For example, the monoclonal antibody may be biotinylated so as to react with avidin complexed with an enzyme or fluorescent compound.

A particular kit embodiment of the invention concerns detection of antibodies against the described Bb 30 kDa antigen, epitopes thereof as represented by portions of the amino acid sequences, or closely related proteins or peptides, such as epitopes associated with other virulence-associated proteins detected by comparison of low-passage, virulent and high-passage, avirulent strains of Bb. The antigen for the kit(s) consists of the Bb 30 kDa protein or portions thereof produced by a recombinant DNA vector in E. coli or another bacterial or nonbacterial host. Alternatively, the antigen may be purified directly from Bb or manufactured as a synthetic peptide. Samples for the assays may be body fluids or other tissue samples from humans or animals. The presence of reactive antibodies in the samples may be demonstrated by antibody binding to antigen followed by detection of the antibody-antigen complex by any of a number of methods, including ELISA, RIA, fluorescence, agglutination or precipitation reactions, nephelometry, or any of these assays using avidin-biotin reactions. The degree of reactivity may be assessed by comparison to control samples, and the degree of reactivity used as a measure of present or past infection with Bb. The assay(s) could also be used to monitor reactivity during the course of Lyme disease, e.g., to determine the efficacy of therapy.

In still further embodiments, the invention contemplates a kit for the detection of Bbnucleic acids in the sample, wherein the kit includes one or more nucleic acid probes specific for the 30 kDa gene, together with means for detecting a specific hybridization between such a probe and Bb nucleic acid, such as an associated label.

BRIEF DESCRIPTION OF THE DRAWINGS

FIG. 1 is a two dimensional gel electrophoresis of low passage (FIG. 1A) and high passage (FIG. 1B) B31 strain of B. burgdorferi, using NEPHGE in the first dimension. Polypeptides either absent or underexpressed in the high passage strain are indicated by $M_r(x\ 10^3)$. These includes polypeptides with $M_r$s of 30,000 (indicated as 30.5 in FIGS. 1A and 1B), 35,000, 24,000 and 20,000. The flagellin, OspA and OspB spots are also indicated. The stain is silver stain.

FIG. 2 shows the immunoreactivity of major B. burgdorferi polypeptides separated by two dimensional gel electrophoresis, as revealed by sequential immunoperoxidase staining with monoclonal antibodies and specific antisera. 2DGE gels prepared as shown above were transferred to PVDF membrane and stained with monoclonal antibodies H68 (specific for OspB), H5332 (OspA), H9724 (41K flagellin) and anti-24K rabbit antiserum. H68 also reacted with a 20K polypeptide(s) in the low passage train, and the anti-24K antiserum also recognized a basic 35K spot (FIG. 2A). The 35K and 20K spots were absent or underexpressed in the high passage strain (FIG. 2B).

FIG. 3 shows the deduced amino acid sequence of low-passage associated 30 kDa protein of Borrelia burgdorferi. The first 140 amino acids are shown in FIG. 3A. FIG. 3B shows amino acids 141 257.

FIG. 4 shows Southern and Northern blot analysis of Bb strain B31 DNA and RNA.

FIG. 5 shows the combined and deduced amino acid sequences of the 30 kDa Bb protein, including putative transcription signals, sequence corresponding to the cyanogen bromide fragment amino acid sequences (underlined) and indicating an open reading frame (FIGS. 5A-5D).

DETAILED DESCRIPTION OF THE PREFERRED EMBODIMENTS

Figure 4A:
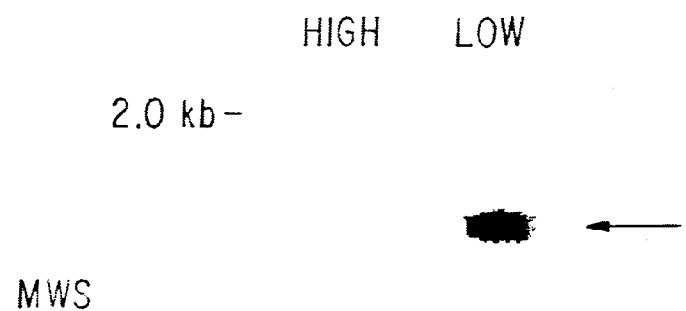
FIG. 4A shows a Southern blot analysis of HindIII digest of DNA from high and low passage isolates of strain B31 probed with an oligonucleotide specific for the 30 kDa protein (SEQ ID NO: 1).

*Borrelia burgdorferi* Strain B31-derived plasmids were deposited on Sep. 18, 1992 with the American Type Culture Collection (ATCC), 12301 Parklawn Drive, Rockville, Md. 20852 USA. The plasmids are identified as pDTB1 (ATCC 75304) and pTBO-87A (ATCC 75305) each containing a partial ospD gene in pUC18 plasmid vector.

The present invention relates to the utility of Bb associated antigenic proteins as diagnostic or preventive tools in Lyme disease. Proteins have been identified as associated only with virulent isolates of Bb, providing a basis for several types of diagnostic tests for Lyme disease, including immunodiagnostic and nucleic acid identification, such as those based on amplification procedures.

The DNA of the present invention was isolated from the bacteria *Borrelia burgdorferi* hereafter designated as Bb. The miroorganism is a spiral-shaped organism approximately 0.2 micron in diameter and ranging in length from about 10-30 microns. Like other spirochetes, it possesses an inner membrane, a thin peptidoglycan layer, an outer membrane, and periplasmic flagella which lie between the inner and outer membranes. Bb is obligate parasite found only in association with infected animals and arthropod vectors in endemic areas. Bb-like organisms have also been identified in birds raising the possibility that birds could also serve as an animal reservoir. While some Bb isolates have been cloned, most isolates have not been cloned and most likely represent mixtures of different variants even at the time of culture origination.

Bb has similarities with other relapsing fever organisms such as *B. hermsii*. Bb has a single chromosome with two unusual features, linear conformation and small size (approximately 900 kilobase pairs). Fresh isolates of Bb contain up to four linear plasmids and six circular supercoiled plasmids. The plasmid content of different Bb isolates is highly variable. For example, in one study only two of thirteen strains had similar plasmid profiles. Some plasmids are lost during in vitro passage which may correlate with loss of virulence. Outer surface proteins OspA and OspB are encoded on the 49 kbp linear plasmid. A 30K virulence-associated protein discovered by the inventors is encoded on a 38 kbp plasmid. Generally, the functions of the Bb plasmids are unknown.

It will be recognized that there is a high degree of variability among Bb, especially among Bb isolates and depending on the number of in vitro passages to which the cultures have been subjected. Generally there are two types of variation that occur among Bb strains; (1) natural heterogeneity present in fresh isolates of Bb, and (2) the artificial changes resulting from in vitro culture. In terms of natural heterogeneity, there is now evidence that at least two distinct populations of Bb exist based on the chromosomal DNA sequences. Primers directed to these DNA sequences indicate two major classes of DNA, one specific to North American Bb isolates, and the other specific for most European isolates. Additionally, primers have been found which recognize all Bb strains. There is significant variability among strains from all geographic locations in terms of plasmid content as well as protein profile, particularly in terms of the molecular weights of the OspA and OspB proteins among European isolates.

In vitro passage of Bb results in loss of plasmids and an apparent concomitant loss of infectivity and virulence in animal hosts. Typically these changes occur within the first 10-17 passages in vitro. It is likely that non-infectious clonal variants begin to occur as soon as Bb is introduced into the "non-selective" in vitro environment and that eventual loss of culture virulence is due to the outgrowth of these variants.

As used herein, Bb isolates have been referred to as "low-passage" or "high-passage". Bb cultures were grown in culture tubes and passaged though various numbers of subcultures. Generally, low-passage isolates underwent 10 or less subcultures while high-passage isolates were cultured often up through 100 passages.

A 30 kDa protein has been identified in low-passage, virulent strains of Bb, but is absent or underexpressed in isogenic high-passage, avirulent strains. Because of the instability of Bb during in vitro culture, it was important that a low passage number ($<10$) strain was available for each isolate and that the virulence of the strain was documented. Virulence was confirmed by inoculating $10^4$ organisms into the backs of 3-week old mice known to be highly susceptible to Bb infection. Using this protocol, low passage, virulent strains of Bb were found to express a major protein not found in avirulent, high passage strains.

Detection of Bb proteins utilized a modification of two dimensional gel electrophoresis. By employing relatively short run times on the gel during the first dimension run, about 4 hrs in comparison to up to 16 hrs in usual isoelectric focusing, protein migration was not at equilibrium, allowing basic proteins especially to focus on the gel and be resolved. The second dimension used was a polyacrylamide gradient SDS-PAGE. Molecular weights were estimated by running molecular weight markers with the solubilized Bb proteins on the gel. This method permitted identification of several polypeptides unique to low passage, virulent Bb strains, including a major protein, an acidic 30K species, as well as a 20K polypeptide. At least one other polypeptide, a 35 kDa protein, appeared to be absent in high passage Bb, implying a possible correlation with virulence or infectivity.

As used herein, DNA segments encoding a polypeptide identified by its approximate molecular weight is referred to by the corresponding number and the letter "K". Thus, as used herein, 30K represents the gene encoding a 30 kDa polypeptde. An alternate designation, also used herein, for the 30K gene is lpa30.

In order to identify DNA segments encoding the 30 kDa protein, purified protein was isolated from a low-passage, virulent *Bb* strain by preparative two dimensional electrophoresis for subsequent use in amino acid sequencing. Initial studies indicated that the N-terminus was blocked. After cyanogen bromide cleavage, separation of the resulting peptide fragments by electrophoresis, and transfer of the peptides to polyvinylene diffusable membranes, sequence analysis was performed using standard sequencing techniques (Matsudaira, 1987). Two of the peptide fragments had overlapping sequences. A 16 amino acid sequence was identified (SEQ ID NO:1). Codons for the amino acid sequence were selected by reverse translation based on (1) conclusion that codons containing A or T were favored and (2) knowledge of published DNA sequences for several *Bb* proteins. A choice favoring A or T containing codons was based on the observation that the G+C content of *Bb* is only 28–35%. A 33 nucleotide segment was synthesized having the structure comprised in SEQ ID NO 1:

AATTTTTTCT AAATCAATTT
CTGCCATTTG TGC

The 33 residue oligonucleotide probe was used as a probe to identify DNA encoding the 30 kDa protein isolated from low-passage, virulent *Bb*. Bacterial cells from low-passage cultures of *Bb* strain B31 were precipitated, lysed and extracted with phenol/chloroform. After HindIII digestion and size distribution on agarose gels, the 0.5 kb band was excised, transferred to another gel and electroeluted. The DNA was incorporated into pUC19 and a library was generated. Clones were isolated, subjected to agarose gel, Southern blot and then hybridized with the radiolabeled oligonucleotide probe. Hybridization occurred with the 87th clone tested.

The oligonucleotide probe hybridized with a 1.0 kb DNA fragment that was isolated by agarose gel electrophoresis. The single clone from which the 1.0 kb DNA was isolated contained a plasmid with a 950 bp insert to which the prepared oligonucleotide probe bound with a 500–600 bp PstI fragment within the insert. The DNA sequence was determined and a deduced amino acid sequence identified. The deduced amino acid sequence is shown in SEQ ID NO:2.

The nucleotide probe was used to determine whether the 30K gene was present and expressed in low-passage isolates of *Bb* from different geographic locations. The probe hybridized with plasmids with apparent sizes from low-passage isolates from HB19 (Connecticut), pKa I (Munich, Germany), and G25 (Sweden). The 30K gene was thus shown to be present in strains from distant geographic regions.

A genomic library has also been prepared from *Bb* strain HB19. This could readily be done for other strains of *Bb* and will be useful in preparing clones for isolating DNA encoding proteins similar or identical with the 30 kDa protein isolated from strain B31. For example, DNA suspected of encoding a virulence associated protein may be genetically transferred, that is, by transfer of DNA into *Bb* via a plasmid with demonstration of production of particular protein expression. Demonstration of virulence using clonal variation would then provide evidence of a causal relationship between the protein and plasmid and virulence.

Testing for virulence was performed by inoculating groups, usually 3–4, of C3H/HeN mice with $\sim 10^6$ organisms. The mice were then observed for joint swelling, bled and sacrificed after 3 weeks. Arthritogenesis, seroconversion and positive cultures from heart, bladder, or other organs provided evidence of virulence. This mouse model appears at present to be the best animal model for Lyme borreliosis (Barthold et al., 1990). Only a few organisms ($\sim 20$) are required to establish infection intradermally, and the mice exhibit chronic, systemic spirochetosis and uniform arthritogenesis and carditis. Other animal models such as rats, hamsters, rabbits, may require high dosages for infection and have relatively mild pathology (Moody et al., 1990). Immunocompromised states (neonatal infection, gamma irradiation) may be necessary to establish infection. Furthermore, it has been shown (Fikrig et al., 1990) that the mouse model may be used to demonstrate both passive and active immunity. C3H/HeN mice may be protected from infection with the N40 strain of *Bb* by injection with anti-OspA monoclonal antibodies and anti-N40 antiserum or immunization with recombinant OspA protein (Fikrig et al., 1990).

Antigenicity of the 30K protein was determined. Antiserum collected from rabbits injected with the protein was shown to react with the 30K protein, as detected on 2-dimensional gel electrophoresis immunoblots of low-passage *Bb* B31. No reactive spots were detected in normal rabbit serum. This result should lead to straightforward production of monoclonal antibodies reactive with the 30K polypeptide and possibly other virulence-associated proteins. Antibodies could be produced in mice and used for screening strains for protein expression, for determining structural location and for examining bactericidal activity of antibodies against these proteins.

It is contemplated that several assays for Lyme disease may be developed using any of the 30K protein or its epitopes, the corresponding DNA encoding the protein, functionally similar proteins and their epitopes, or by detection of the appropriate mRNA. An indirect ELISA assay is set forth in Example 9 and could be used with the 30 kDa protein or other antigenic *Bb* proteins, such as the 20K protein. These methods are similar in principle to those previously described (Magnarelli et al., 1989; Magnarelli et al., 1984; and Craft et al., 1984). Reactive epitopes representing portions of the 30 kDa protein sequence could be utilized in an analogous manner.

Another promising assay is the microcapsule agglutination technique (MCAT) (Arimitsu et al., 1991). In this procedure, microscopic polystyrene beads are coated with *Bb* antigen and incubated with dilutions of patient serum. After overnight incubation at 4° C., the agglutination patterns are determined. Using whole *Bb* as antigen, the MCAT has been shown to be highly discriminatory between Lyme disease patients and healthy individuals, with little overlap in agglutination titer, although false positive reactions have been obtained with rheumatoid arthritis patients (Anderson et al., 1988; and Centers Dis. Control, 1988) and leptospirosis samples (Barbour, 1988; and Centers for Disease Control, 1989). An assay using 30 kDa protein alone or in combination with other antigens such as the 94K, 30K and 21K antigens should be feasible. Such combination may increase sensitivity of the assay.

The invention has disclosed a DNA segment encoding an antigenic protein that is apparently associated only with virulent strains of *Bb*. Detection of that DNA or various parts thereof is expected to provide the basis for a useful assay. One method of detecting the 30 kDa antigen gene is based on selective amplification of known portions of the gene. A particular method utilizes PCR amplification, using any of a number of primers that could be prepared from knowledge of the nucleic acid sequence of SEQ ID NO:1, FIG. 5. Generally, such primers are relatively short, e.g., 7-28 base pairs in length, and may be derived from the respective sense or anti-sense strands of the disclosed DNA segment. Synthesis of these primers may utilize standard phosphoramidite chemistry (Beaucage et al., 1981).

Part of the present invention contemplates vaccine preparation and use. General concepts related to methods of preparation and use are discussed as applicable to preparations and formulations with the disclosed 30 kDa antigen, its epitopes and subfragments thereof.

VACCINE PREPARATION AND USE

Preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10-95% of active ingredient, preferably 25-70%.

The proteins may be formulated into the vaccine as neutral or salt forms. Pharmaceutically acceptable salts include acid addition salts (formed with the free amino groups of the peptide) and which are formed with inorganic acids such as, for example, hydrochloric or phosphoric acids, or such organic acids as acetic oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine include use of agents such as aluminum hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperatures ranging between 70° to 101° C. for 30 second to 2 minute periods respectively. Aggregation by reactivating with pepsin treated (Fab) antibodies to albumin, mixture with bacterial cells such as *C. parvum* or endotoxins or lipopolysaccharide components of gramnegative bacteria, emulsion in physiologically acceptable oil vehicles such as mannide mono-oleate (Aracel A) or emulsion with 20 percent solution of a perfluorocarbon (Fluosol-DA) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1-5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

The invention also contemplates the use of disclosed nucleic acid segments in the construction of expression vectors or plasmids and use in host cells. The following is a general discussion relating to such use and the particular considerations in practicing this aspect of the invention.

HOST CELL CULTURES AND VECTORS

In general, of course, prokaryotes are preferred for the initial cloning of DNA sequences and constructing the vectors useful in the invention. For example, in addition to the particular strains mentioned in the more specific disclosure below, one may mention by way of example, strains such as *e. coli* K12 strain 294 (ATCC No. 31446), *E. coli* B, and *E. coli* X 1776 (ATCC No. 31537). These examples are, of course, intended to be illustrative rather than limiting.

Prokaryotes are also preferred for expression. The aforementioned strains, as well as *E. coli* W3110 (F-, lambda-, prototrophic, ATCC No. 273325), bacilli such as *Bacillus subtilus*, or other enterobacteriaceae such as *Salmonella typhimurium* or *Serratia marcesans*, and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (see, e.g., Bolivar et al., 1977). The pBR322 plasmid contains genes for ampicillin and tetracycline resistance and thus provides easy means for identifying transformed cells. The pBR plasmid, or other microbial plasmid or phage must also contain, or be modified to contain, promoters which can be used by the microorganism for expression.

Those promoters most commonly used in recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1979; EPO Appl. Publ. No. 0036776). While these are the most commonly used, other microbial promoters have been discovered and utilized, and details concerning their nucleotide sequences have been published, enabling a skilled worker to ligate them functionally with plasmid vectors (Siebwenlist et al., 1980). Certain genes from prokaryotes may be expressed efficiently in *E. coli* from their own promoter sequences, precluding the need for addition of another promoter by artificial means.

In addition to prokaryotes, eukaryotic microbes, such as yeast cultures may also be used. *Saccharomyces cerevisiase*, or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (Tissue Culture, 1973). Examples of such useful host cell lines are VERO and HeLa cells, Chinese hamster ovary (CHO) cell lines, and W138, BHK, COS-7 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BgII site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Also contemplated within the scope of the present invention is the use of the disclosed DNA as a hybridization probe. While particular examples are provided to illustrate such use, the following provides general background for hybridization applications taking advantage of the disclosed nucleic acid sequences of the invention.

NUCLEIC ACID HYBRIDIZATION EMBODIMENTS

As mentioned, in certain aspects, the DNA sequence information provided by the invention allows for the preparation of relatively short DNA (or RNA) sequences having the ability to specifically hybridize to *B. burgdorferi* gene sequences. In these aspects, nucleic acid probes of an appropriate length are prepared based on a consideration of the sequence, e.g., as shown in FIG. 5 SEQ ID NO:1 or derived from flanking regions of these genes. The ability of such nucleic acid probes to specifically hybridize to the *B. burgdorferi* gene sequences lend them particular utility in a variety of embodiments. Most importantly, the probes can be used in a variety of diagnostic assays for detecting the presence of pathogenic organisms in a given sample. However, either uses are envisioned, including the use of the sequence information for the preparation of mutant species primers, or primers for use in preparing other genetic constructs.

To provide certain of the advantages in accordance with the invention, the preferred nucleic acid sequence employed for hybridization studies or assays includes sequences that are complementary to at least a 10 to 40, or so, nucleotide stretch of the selected sequence, such as that shown in FIG. 5 or SEQ ID NO:1. A size of at least 10 nucleotides in length helps to ensure the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. Thus, one will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production.

The present invention will find particular utility as the basis for diagnostic hybridization assays for detecting Bb-specific RNA or DNA in clinical samples. Exemplary clinical samples that can be used in the diagnosis of infections are thus any samples which could possibly include nucleic acid, including samples from tissue, blood serum, urine or the like. A variety of tissue hybridization techniques and systems are known which can be used in connection with the hybridization aspects of the invention, including diagnostic assays such as those described in Falkow et al., U.S. Pat. No. 4,358,535.

Accordingly, the nucleotide sequences of the invention are important for their ability to selectively form duplex molecules with complementary stretches of *B. burgdorferi* gene segments. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids, for example, one will select relatively low salt and/or high temperature conditions, such as provided by 0.02M–0.15M NaCl at temperatures of 50° C. to 70° C. These conditions are particularly selective, and tolerate little, if any, mismatch between the probe and the template or target strand.

Of course, for some applications, for example, where one desires to prepare mutants employing a mutant primer strand hybridized to an underlying template, less stringent hybridization conditions are called for in order to allow formation of the heteroduplex. In these circumstances, one would desire to employ conditions such as 0.15 M-0.9 M salt, at temperatures ranging from 20° C to 55° C. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In clinical diagnostic embodiments, nucleic acid sequences of the present invention are used in combination with an appropriate means, such as a label, for determining hybridization. A wide variety of appropriate indicator means are known in the art, including radioactive, enzymatic or other ligands, such as avidin/biotin, which are capable of giving a detectable signal. In preferred diagnostic embodiments, one will likely desire to employ an enzyme tag such as alkaline phosphatase or peroxidase, instead of radioactive or other environmentally undesirable reagents. In the case of enzyme tags, colorimetric indicator substrates are known which can be employed to provide a means visible to the human eye or spectrophotometrically, to identify specific hybridization with pathogen nucleic acid-containing samples. Luminescent substrates, which give off light upon enzymatic degradation, could also be employed and may provide increased sensitivity.

In general, it is envisioned that the hybridization probes described herein will be useful both as reagents in solution hybridization as well as in embodiments employing a solid phase. In embodiments involving a solid phase, the test DNA (or RNA) from suspected clinical samples, such as exudates, body fluids (e.g., amniotic fluid cerebrospinal fluid) or even tissues, is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

The present invention has addressed the cloning of nucleic acids encoding certain antigenic polypeptides related to a 30 kDa protein. Identification of virulence-associated proteins in addition to the 30 kDa antigenic protein should be possible using methods analogous to those disclosed herein. One method would be to produce a cDNA library using mRNA obtained from low-passage isolates. Although the production of cDNA libraries from bacteria is not commonly done because of the usual absence of poly-A tails on prokaryotic messages, a cDNA library has been constructed from *Borrelia hermsii* mRNA. The technique involves use of random primers and reverse transcriptase to produce the initial cDNA. From that point linkers are attached and the inserts cloned into a suitable plasmid or bacteriophage vector. This technique lends itself also to use with "subtraction" techniques. In this way, DNA from a high-passage, non-infectious isogenic isolate can be used to hybridize transcripts common to high and low-passage isolates out of the mRNA.

A method of preparing variants of the 30 kDa antigen is site-directed mutagenesis. This technique is useful in the preparation of individual peptides, or biologically functional equivalent proteins or peptides, derived from the OMP antigen sequence, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art.

In general, site-directed mutagenesis in accordance herewith is performed by first obtaining a single-stranded vector which includes within its sequence a DNA sequence which encodes the 30 kDa antigen. An oligonucleotide primer bearing the desired mutated sequence is prepared, generally synthetically, for example by the method of Crea et al. (1978). This primer is then annealed with the single-stranded vector, and subjected to DNA polymerizing enzymes such as $E.$ $coli$ polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as $E.$ $coli$ cells, and clones are selected which include recombinant vectors bearing the mutated sequence arrangement.

The preparation of sequence variants of the selected 30K gene using site-directed mutagenesis is provided as a means of producing potentially useful 30K species and is not meant to be limiting as there are other ways in which sequence variants of the 30K gene may be obtained. For example, recombinant vectors encoding the desired 30K gene may be treated with mutagenic agents to obtain sequence variants (see, e.g., a method described by Eichenlaub, 1979) for the mutagenesis of plasmid DNA using hydroxylamine.

The following examples are intended to illustrate the practice of the present invention and are not intended to be limiting. Although the invention is demonstrated with a 30 kDa protein from $Bb,$ other antigenic proteins unique to virulent strains might be used in a similar fashion. The proteins identified and the encoding DNA are clearly useful in developing selective and sensitive assays for Lyme disease and in potentially distinguishing virulent infections of $Bb$ in humans.

EXAMPLE 1

The present example illustrates the differences in polypeptides produced in low-passage, virulent strains of $Bb$ and those produced in isogenic, high passage, a virulent strains. This was intended to identify proteins essential for infectivity and virulence of $Bb$ in mammalian hosts. Because different isolates are likely to possess differences unrelated to virulence, comparisons were performed between well-defined, low passage strains and the same strains following prolonged in vitro passage.

One of the initial problems in separating $Bb$ proteins was the loss of several major proteins, including OspA and OspB, when standard 2-dimensional gel electrophoris was employed. This loss occurred from the cathodic end and was apparently due to cathodic drift. A modification of isoelectric focusing called nonequilibrium pH gradient electrophoresis (NEPHGE) (O'Farrell et al., 1977) was successful in resolving all major $Bb$ polypeptides. This technique utilizes shorter run times so that all polypeptides ar retained in the gel pattern.

NEPHGE OF VIRULENT AND AVIRULENT STRAINS OF $Bp$

The B31 strain of $Bb$ was passaged in BSKII medium and incubated at 34° C. until late log phase (7-10 days). Low passage was less than 10 passages while high passage was >100 in vitro passages. For protein analysis, $Bb$ from late log phase cultures was washed three times by centrifugation and gently resuspended in phosphate-buffered saline and stored at $-70°$ C. Organisms ($2 \times 10^8$ per gel) were sonically disrupted, suspended in solubilization buffer and subjected to NEPHGE in 3 mm tube gels. NEPHGE differed from standard 2-dimensional gel electrophoresis primarily in the duration of electrophoresis. Run time was 4 hrs at 400 volts, as opposed to 16 hrs for isoelectric focusing (IEF). Since protein migration was not at equilibrium, many proteins not focused on standard IEF were resolved. The second dimension gel consisted of SDS-PAGE with an 8 to 20 percent polyacrylamide gradient to enhance separation. Single dimension lanes containing solubilized $Bb$ and molecular weight standards (BioRad, Richmond, Calif.) were placed on either end of the tube gel. Polypeptides were visualized by silver staining; alternatively, the 2-dimensional gel electrophoresis pattern was transferred to a PVDF membrane for immunoblot analysis (Matsudaira, 1987).

The pattern of gel spots was highly reproducible, permitting unambiguous identification of most moderate to high concentration polypeptides. Gel patterns were compared visually to detect qualitative similarities and differences. Although not employed for measurements, it is contemplated that quantitative analysis could be carried out using a Visage 2000 Image Analysis system (BioImage, Ann Arbor, Mich.). The instrument densitometer/computer system is used to scan, store, and interpret an image array of $1024 \times 1024$ pixels (0.18 mm$^2$/pixel). Two-dimensional gel electrophoresis (2DGE) spot identification, alignment and quantification data are collected and analyzed utilizing a Visage Image Analysis software package.

FIG. 1 shows a comparison between low passage and high passage isolates of the B31 strain of $Bb;$ these strains were subjected to less than 5 and greater than 100 in vitro passages, respectively. Over 100 spots were detected by silver staining in each pattern, but the 2D pattern was dominated by a few major structural proteins, as was also the case with $T.$ $pallidum.$ Streaking of the major spots toward the origin of migration (the acid end) occurred due to the non-equilibrium nature of the NEPHGE separation. OspA, OspB, and the 41K flagellin were identified by $M_r$ and by their reactivities with monoclonal antibodies (FIG. 2). The MoAb H68 also reacted with a series of 20K spots in the low passage isolate, indicating the presence of shared epitopes between OspB and the 20K polypeptide. Rabbit antiserum against a 24K polypeptide reacted with a major spot in low passage B31; this anti-serum also reacted with a basic 35K polypeptide.

The most noticeable difference low passage and high passage B31 was the presence of a major, acidic polypeptide with an $M_r$ of 30,500 in the low passage isolet. This polypeptide, called the 30K protein, lies just below OspA in the SDS PAGE dimension and therefore was not well separated from OspA in most published SDS PAGE patterns. There was no evidence of a 30K polypeptide in the high passage B31. The 20K polypeptide reactive with MoAb H68 was also absent from high passage B31. The 24K protein was expressed in smaller quantities, whereas the basic 35K polypeptide which reacted with the anti-24K anti-serum was not detectable in the high passage isolate. Similar results were obtained with well-defined low and high passage variants of the North American human blood isolate HB19 (not shown).

EXAMPLE 2

The observation of a polypeptide found in low passage *Bb* but not detectable in high passage *Bb* strain B31 led to efforts to isolate and characterize this apparently unique protein. The protein, as indicated in Example 1, was a major, acidic protein that was suspected of being associated with virulence.

PURIFICATION AND PARTIAL SEQUENCE DETERMINATION OF THE 30K PROTEIN

Approximately 5 micrograms of the 30K protein was purified from low passage B31 by large scale two-dimensional electrophoresis, as developed for the purification of *T. pallidum* polypeptides (Norris et al., 1988). $10^{10}$ *Bb* were solubilized, loaded onto 24 tube gels, and subjected to NEPHGE. The tube gels were stained with Coomassie blue G, and the protein band corresponding to the 30K protein, as determined by comparing to a 2D gel pattern, was carefully sliced out. The excised bands were equilibrated with SDS PAGE buffer, and electrophoresed together on a single SDS PAGE gel. The Coomassie blue stain spots representing purified 30K protein were excised and electroeluted. Initial studies showed that the N-terminus was blocked so a preparation of the 30K protein was treated with cyanogen bromide to cleave the protein internally at methionine residues. The resulting fragments were separated on a 20% acrylamide SDS page gel and transferred to a PVDF membrane for sequence analysis (Matsudaira, 1987). N-terminal sequence was obtained from two prominent peptides which had similar $M_r$'s. These turned out to be overlapping peptides due to the presence of two methionine residues separated by only five intervening amino acids. The additive sequence obtained from these two peptides was as follows:

X X Leu Ala Gln Met Ala Glu Ile Asp Leu Glu Lys Ile X Asn where X represents an undetermined amino acid residue.

EXAMPLE 3

After determining partial amino acid sequence of a *Bb* protein that appeared to be unique to virulent, low passage strains of *Bb* strain B31, see Example 2, it was desired to develop a means to detect DNA sequences in B31 and other strains. This was achieved by synthesizing an oligonucleotide probe, derived from the amino acid sequence determined from the 30 kDa protein using the most common codon usage observed in the *Bb* genes that had already been sequenced (see Example 2).

DNA HYBRIDIZATION

The nucleotide sequence shown below is derived from the 30K amino acid sequence using the most common codon usage observed in the *Bb* genes sequenced. G+C content of *Bb* is 28-30%. Thus codons containing A or T are highly favored.

AATTTTTTCT AAATCAATTT
CTGCCATTTG TGC

The radiolabeled nucleotide was used as a probe to determine whether complementary sequences were present in Southern blots of whole, genomic *Bb* DNA from low passage and high passage B31. Under conditions of low stringency, the oligonucleotide hybridized with a HindIII DNA fragment present in low passage B31 but not high passage B31, see FIG. 3.

Figure 4B:
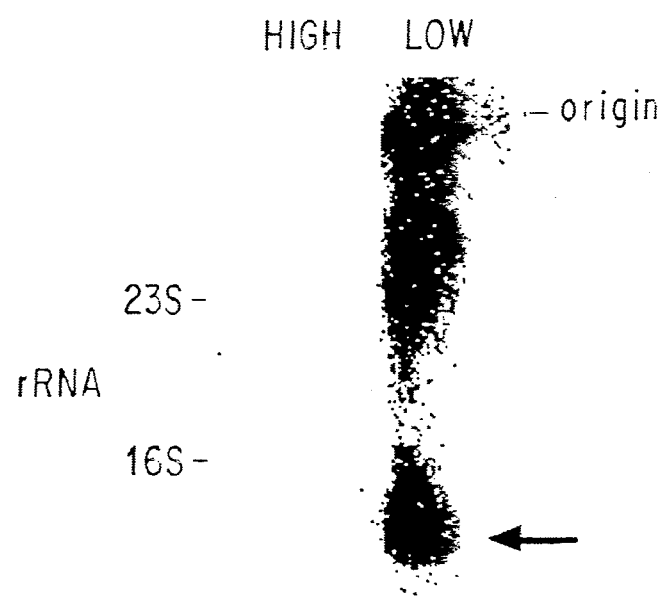
FIG. 4B shows a Northern blot analysis of total RNA from high and low passage isolates of strain B31 probed with 30 kDa protein-specific oligonucleotide.

The 30K encoding sequence was localized to a plasmid with an apparent size of 38 kilobase pairs, using DNA hybridization of the oligonucleotide to Southern blots of *Bb* plasmid preparations. This plasmid appeared to be linear; high passage strains lacking the 30K protein were also missing the 38 kbp plasmid. The 30K oligonucleotide did not hybridize to Southern blots of plasmid preparations from these strains. Northern blots confirmed that an mRNA species that hybridized with the above probe was expressed in low passage B31 strains but not in high passage strains (see FIG. 4). The oligonucleotide was also found to hybridize to similar plasmids in several other low passage *Bb* isolates, including HB-19 (human blood isolate, U.S.), PB1 and Munich86 (human cerebrospinal fluid isolates, Germany), G25 (Sweden), and Veery (U.S. bird isolate). No corresponding plasmid was found in high passage strains of *Bb* or in *Borrelia hermsii*.

EXAMPLE 4

The hybridization of the oligonucleotide probe of Example 2 with a HindIII DNA fragment associated with low passage *Bb* strain B31 but not with high passage B31, strongly implicated the DNA as encoding the 30 kDa polypeptide typically associated with low passage *Bb* strains. Therefore, molecular cloning of the DNA was undertaken.

MOLECULAR CLONING OF THE 30K GENE

To facilitate the cloning of the 30K gene, HindIII fragments were size selected by agarose gel electrophoresis, and bands between 0.5 and 2.0 kilobase in size were electroeluted. These fragments were ligated into the plasmid pUC19 which had been cleaved with HindIII and dephosphorylated. *E. coli* strain Jm109 was transformed with the recombinant plasmids, and the resulting recombinants were screened by hybridization with the oligonucleotide under conditions of low stringency. After repeated screening, a single clone (pTB087A) that hybridized to the oligonucleotide was isolated. TB087A contained a 950-bp *Bb* DNA insert, and the oligonucleotide was bound to a 500-600 PstI fragment within this insert. 80% of the 30K gene and an additional 300 base pairs of upstream, untranslated DNA was obtained. An additional 1.5 kb PstI fragment containing the remainder of the 30K gene was cloned into pUC19.

Dideoxynucleotide sequencing of clone Tbo87 demonstrated the presence of an extended open reading frame encoding 257 amino acids, FIG. 3, SEQ ID NO. 2. Typical −35 and −10 σ70 recognition sites and Shine Delgarno ribosome binding site sequences were found upstream of the presumed start codon (underlined). Several additional −35 and −10 sequences were found further upstream, possibly indicating unusual transcriptional regulation mechanisms.

The N-terminal region of the deduced amino acid sequence was typical of the signal peptides of bacterial lipoproteins. The N-terminal methionine was followed by a cluster of lysine residues, a hydrophobic region and a signal peptidase 2 (SP2) recognition sequence. The latter sequence, Leu Ser Ile Ser Cys, differed somewhat from the consensus SP2 recognition sequence (Leu Xaa Xaa Cys) found in most bacteria, but closely resembled the cleavage sequence Leu Met Ile Gly Cys of the variable major proteins Vmp7 and Vmp21 of *B. hermsii*. These variable surface antigens of relapsing fever organisms have been shown to be lipoproteins (Burman et al, 1990). The presence of this leader sequence implied the mature 30 kDa protein is translocated across the cytoplasmic membrane and is anchored to the cytoplasmic membrane and/or outer membranes via fatty acids associated with an N-terminal cysteinyl residue.

The Tbo87 clone containing 30K gene was identified by hybridization with an oligonucleotide sequence based on a CNBr fragment amino acid sequence. A sequence corresponding exactly to the CNBr cleavage fragment was identified as residues 119-129 in the deduced amino acid sequence, confirming the identity of the gene. The oligonucleotide used for screening was identical at 30 of 33 positions.

Figure 7:
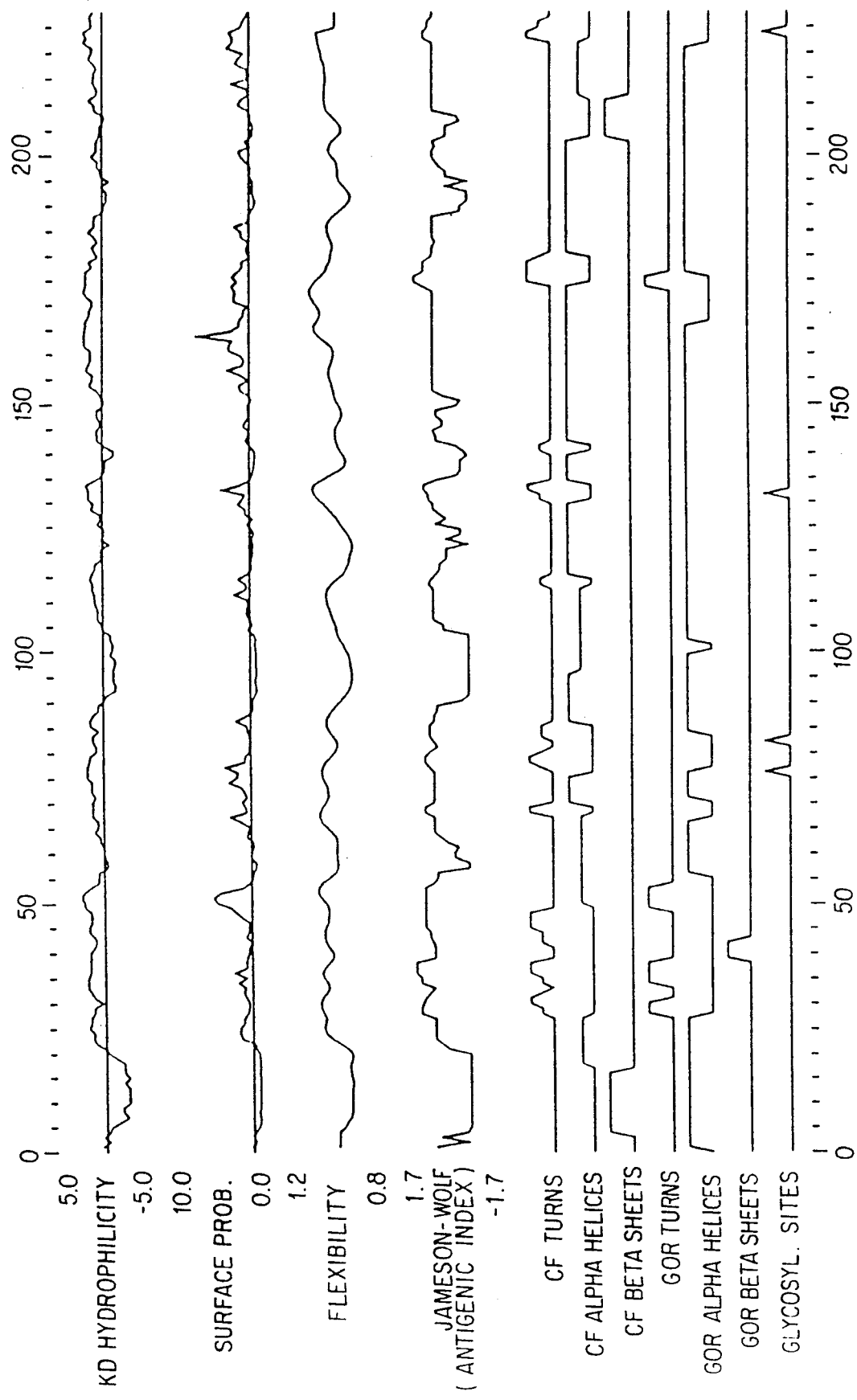
FIG. 7 is a composite of several plotstructures indicating results of various measurements on the 30 kDa Bb polypeptide. The analyses were run on a 227 amino acid sequence of the 30 kDa polypeptide.

Analysis of the secondary structure of the gene was conducted using the method of Garnier et al., 1978. An alpha helical structure for over 90% of the sequence was predicted. Plots showing α-helix and β-sheet analyses are shown in FIG. 7. Glycosylation sites are also indicated in the plotstructure shown in FIG. 7.

Figure 6:
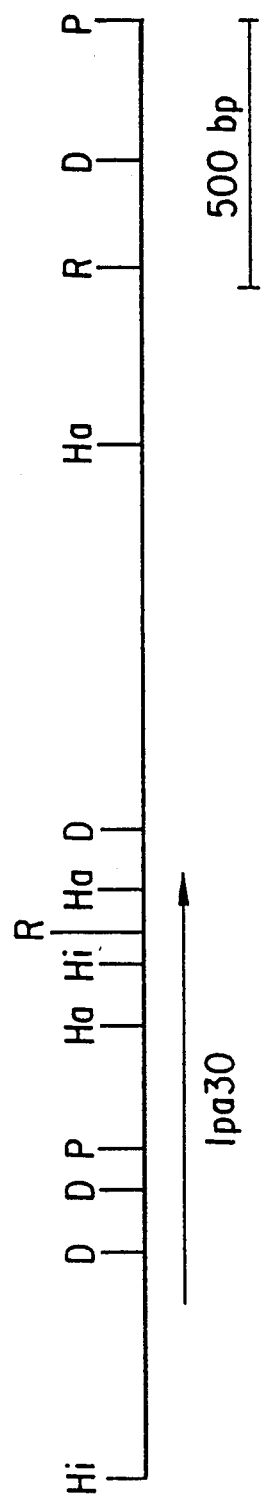
FIG. 6 shows a restriction map of the 30K DNA segment cloned. Lpa 30 indicates the location and orientation of the 30K gene (the gene encoding the 30 kDa polypeptide from Bb ). The region between the two HindIII sites on the left end represents the original clone, Tbo87. The second region cloned to obtain the remainder of the 30K sequence is between the two PstI sites. The abbreviations used for the restriction endonucleases are: Hi=HindIII; D=DraI; P=PstI; Ha=HaeIII; and R=RsaI.

A restriction map of the cloned DNA is shown in FIG. 6. Ipa30 indicates the location and orientation of the 30K gene. The region between the two HindIII sites on the left represents clone Tbo87. The cloned region between the PstI sites represents the region cloned to obtain the remainder of the 30K sequence.

EXAMPLE 5

The presence of the 30K gene in low passage, virulent strains of *Bb* obtained from different geographic locations was examined, with the intention of determining the generality of existence of this gene and its associated 30 kDa associated gene product. All strains tested indicated the presence of this gene, indicating a strong association of the 30 kDa protein with virulence.

PRESENCE OF THE 30K GENE IN VIRULENT *B. burgdorferi* ISOLATES

The 30K oligonucleotide described in Example 3 was hybridized with plasmids having apparent sizes of 38-40 kilobase from several low passage isolates including HB19 (Connecticut), PB1, Munich 86, and PKA1 (Germany), and G25 (Sweden). Plasmids were isolated, purified, run on an agarose gel followed by Southern blot and hybridized with the oligonucleotide probe prepared as described by Barbour, (1988). The 30K gene was thus shown to be present in strains from a variety of geographic regions. The 30K protein was expressed by HB19 in a quantity similar to that found in B31.

EXAMPLE 6

Genomic DNA libraries may be prepared from several *Bb* strains and DNA sequences compared. This would assist in identifying other virulence specific antigens and in determining the underlying molecular basis of virulence associated with *Bb*. The following example illustrates preparation of a genomic library from *Bb*, strain HB19.

GENOMIC LIBRARY FROM A LOW PASSAGE INFECTIOUS ISOLATE OF *B. burgdorferi*

A low passage isolate of a human blood isolate (Steere et al., 1983) was used to prepare a genomic library. This isolate had been shown to be infectious for rats and mice. This was confirmed by successfully infecting scid mice with this isolate. Four mice were inoculated intraperitoneally with $10^7$ spirochetes. Blood was cultured weekly in BSK II medium (Barbour, 1984) and blood, bladder, and spleens were cultured after euthanasia at three weeks. All mice were shown to be spirochetemic at each culture and at autopsy. When high passage isolate of the HB19 was inoculated at the same inoculum into scid mice, none of the mice showed evidence of infection after culture of blood or at autopsy.

The low passage HB19 isolate was grown in BSK II medium. Total DNA was extracted using a phenol/chloroform extraction and standard techniques (Hinnebusch et al., 1990). A genomic DNA library was prepared using lambda cloning factor FIXII (Strategene, La Jolla, Calif.). Total DNA from low passage HB19 was partially digested with Sau3A and ligated with lambda arms with partially filled XhoII ends. The s*Bb* selection provided for the cloning of 15-23 kbp inserts of borrelia DNA in the vector; $3.9 \times 10^6$ primary plaques on P2 lysogen were obtained. The vector alone produced no plaques when plated on a P2 selective host.

Total DNA content of *B. burgdorferi* was approximately 1100 kilobases. The size of the library was considered sufficient on a statistical basis to be representative of the entire genome. The library was screened with probes for the genes for OspA, OspB (Bergström et al., 1989) and for the flagellin protein (Sadziene et al., 1991). Clones containing hybridizing sequences for each of these probes were present in the phage library at a frequency between $10^{-2}$ and $10^{-3}$, leading to the conclusion that the phage library was likely representative of the genome.

EXAMPLE 7

It was shown in Example 1 that a major 30 kDa polypeptide was associated with a low passage, virulent strain of *Bb*. A remaining question was whether or not this polypeptide was antigenic and therefore might be useful in developing specific antibodies to *Bb* for diagnostic purposes and vaccine development. This example demonstrates that the 30 kDa polypeptide isolated from low passage, virulent *Bb* strain induces an antibody response in rabbits.

ANTIGENICITY OF THE 30K PROTEIN

Rabbits were immunized by injections at bi-weekly intervals with the 30 kDa protein obtained from *Bb*, strain B31. Each rabbit was injected with 5 μg antigen (1.7 μg/kg) in distilled water. The antigen was purified by two-dimensional electrophoresis and emulsified in complete Freunds adjuvant (first injection) and incomplete Freunds adjuvant (subsequent injections). Antiserum from this rabbit reacted with a spot corresponding to the 30 kDa protein from *Bb*, strain B31, in two-dimensional gel electrophoresis immunoblots of low passage B31, whereas normal rabbit serum did not react. The reactive spot was not detected in 2DGE immunoblots of high passage B31. Both the anti-30 kDa antiserum and normal rabbits serum possessed background reactivity with several *B. burgdorferi* polypeptides.

EXAMPLE 8

This example illustrates the contemplated use of the 30 kDa protein to generate antibodies. While the example illustrates preparation of a monoclonal antibody, polyclonal antibodies or other monoclonals, developed from epitopic regions of the 30 kDa polypeptide are readily obtainable by similar procedures.

MONOCLONAL ANTIBODIES TO *Bb* 30 kDa POLYPEPTIDE

Monoclonal antibodies are prepared following in general the procedure of Goding (1980) Purified 30 kDa *Bb* polypeptide is combined with DNA/cellulose and taken up in Freund's complete adjuvant for the initial immunization. Subsequent immunizations utilize incomplete Freund's adjuvant. BALB/C mice are immunized intraperitoneally initially, then intramuscularly. Blood is checked for testing of antibody production. High antibody titer animals are selected and the spleen removed, minced and cells isolated and tested for viability. Splenic lymphocytes are then fused with a nonsecretor myeloma cell line such as $P_3$-NS1-Ag4-1 obtained from a commercial source, using PEG to induce cells to fuse. Cells are plated and HAT media used for feeding cultures. Cells are weaned from growth on serum after 2 or more clonings.

Preliminary screening is accomplished by an ELISA. A hybridoma screening kit may be used (e.g., BRL, Bethesda, Md.). Plates are coated with goat serum and then hybridoma culture supernatant added to control plates and to plates previously coated with 30 kDa antigenic polypeptide. After incubation, plates are washed and β-galactosidase conjugated goat anti-mouse antibody 1:200 dilution in PBS containing 1% goat serum (BRL reagent) added and further incubated. A chromophoric substance, p-nitrophenyl glucose is added and incubation continues for about 1 hr followed by quenching by addition of sodium carbonate solution. Well are read at 410 nm on an ELISA plate reader. A positive reaction is indicated by development of a yellow color in the well.

Cells are cloned from positive wells by plating at 0.5-2 cells per well with later recloning at 0.3 to 0.5 cells per well. Positive clones are recognized by a screening method similar to that used for hybridomas. Isotyping of cells is achieved using a Boehringer Mannheim Biochemicals-mouse immunoglobulin subtype identification kit. Two antigens are used to coat the plates. Cappel's affinity purified goat anti-mouse IgG-heavy and light chain at a 1:50 dilution are used. The second antigen is the 30 kDa antigenic *Bb* polypeptide. Once the hybridoma cells are successfully cloned, they may be grown in bulk. Antibody concentrations that might be expected are 10–100 μl/ml.

EXAMPLE 9

This example illustrates a contemplated immunodiagnosis for detection of Lyme disease. This particular example is based on an ELISA type assay, but other types of immunoassays are also contemplated. It will be appreciated that the availability of a protein specific for virulent forms of Lyme disease and monoclonal antibodies to that protein or epitopes having antigenic properties enables development of specific tests for the disease so that immunoassays are not limited to use of the 30 kDa antigen.

ELISA ASSAY FOR LYME DISEASE

The 30 kDa protein or portions thereof will be produced in large quantities by recombinant DNA vectors and purified. Alternatively, synthetic peptides could be used as antigen. Optimal concentration of the antigen will be determined by checkerboard titration, using serial two-fold dilutions. The antigen in 50 μl of distilled water or 0.05 M $NaHCO_3$ will be added to polystyrene microtiter plates and allowed to dry by incubation for 18-20 hrs at 37° C. Wells incubated with buffer alone will serve an antigen controls. Plates will be washed 3 times with PBS-0.05% Tween 20 prior to use. Two-fold dilutions (60 μl per well) of the three serum pools described above in PBSTween will be tested in triplicate, using 1:25 as the starting dilution. After incubation for 1 hr at 37° C. in a humidified chamber, the plates will be washed 5 times and incubated with the optimal dilutions of goat anti-human IgM or anti-human IgG alkaline phosphatase conjugates (1:500 to 1:2000). p-Nitrophenyl phosphate will be used as the substrate, and the reaction stopped at 30 min with 50 μl 3 N NaOH. Absorbance will be measured at 405 nm using a Dynatech ELISA reader. PBS-Tween will be used as the diluent throughout; the possible background-damping effects of using the more complex dilution buffer (Magnarelli et al., 1984) for the blocking step and throughout all the incubation steps will be evaluated. Standard immunofluorescence assay (IFA) and ELISA assays using whole *Bb* will be used for comparison. Depending on the reproducibility of results obtained with repeated ELISAs, reactivity cutoffs will be established as either a certain difference in absorbance (e.g., 0.2) over the negative control wells, or 3 standard deviations above the negative control wells. The titer of a serum will be defined as the reciprocal of the last dilution showing reactivity.

Once optimal conditions are established, a panel of ~100 well-defined sera, potentially including documented true-positive (early and late infections), true negative, false positive and false-negative sera, will be tested for reactivity and compared to the results of the IFA and whole *Bb* ELISA assays. Immunoblot reactivity will also be determined. Specificity and sensitivity of the 30K assay may be examined further by testing sera from mice at different stages of infection and infected with different strains of *Bb*. These results would indicate the relative course for seroconversion for each of the assays and would also show whether infection with different strains causes variation in anti-30K titers.

Figure 8:
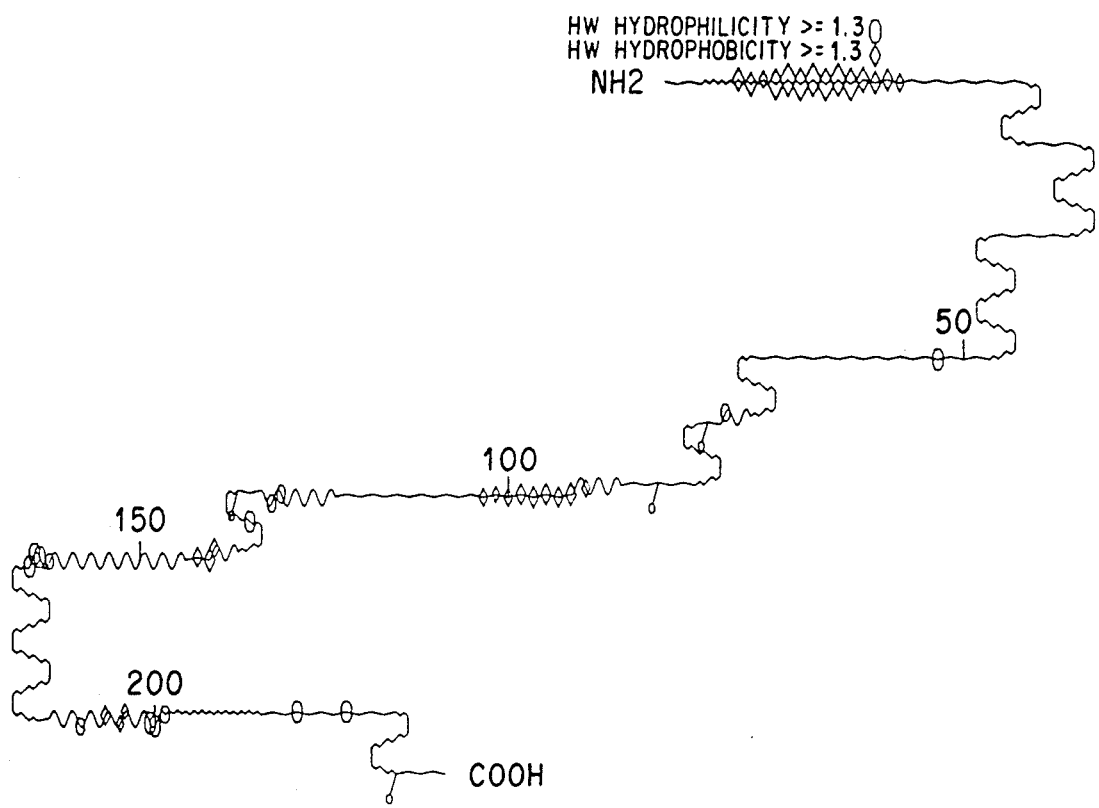
FIG. 8 is a plotstructure showing a Chou-Fasman hydrophilicity/hydrophobicity prediction analysis of the 30 kDa Bb polypeptide. Oblongated circles represent regions of predicted hydrophilicity $\geq 1.3$ while diamond symbols represent regions of predicted hydrophobicity $\geq 1.3$.
Figure 9:
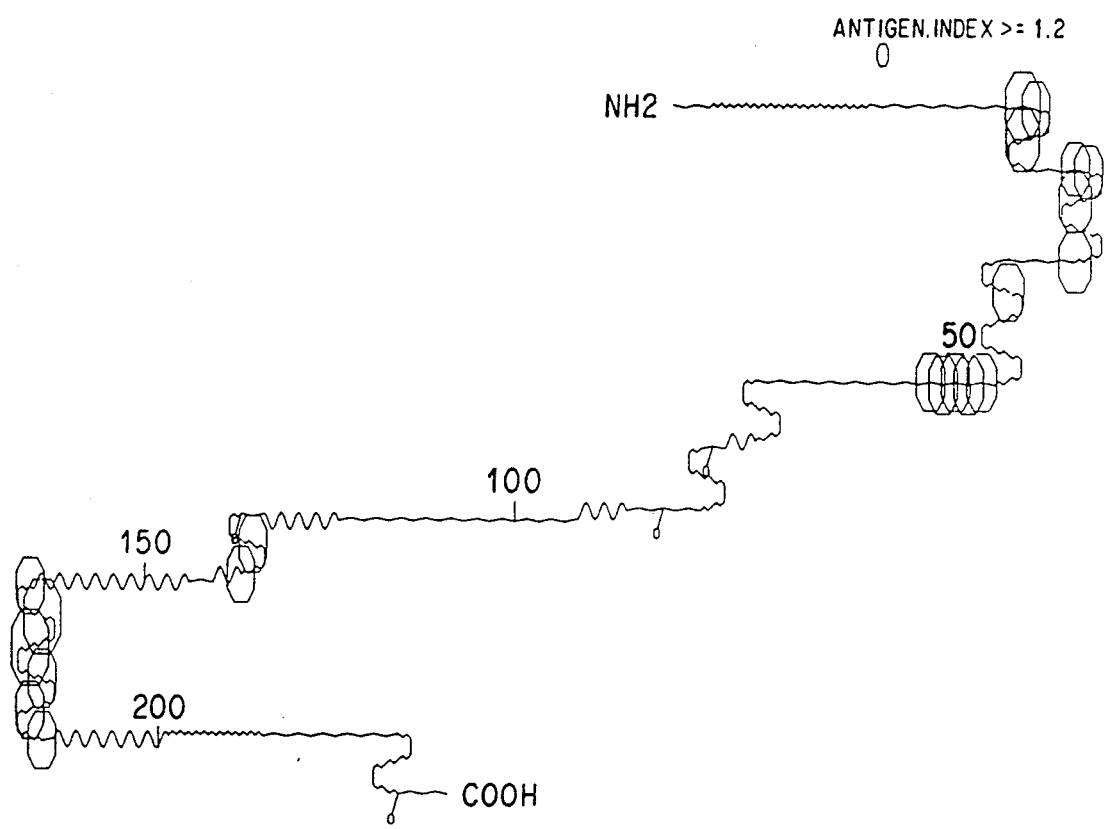
FIG. 9 shows a plotstructure representing a Chou-Fasman antigen index for the 30 kDa Bb polypeptide. Oblongated circles represent an antigen index $\geq 1.2$.
Figure 10:
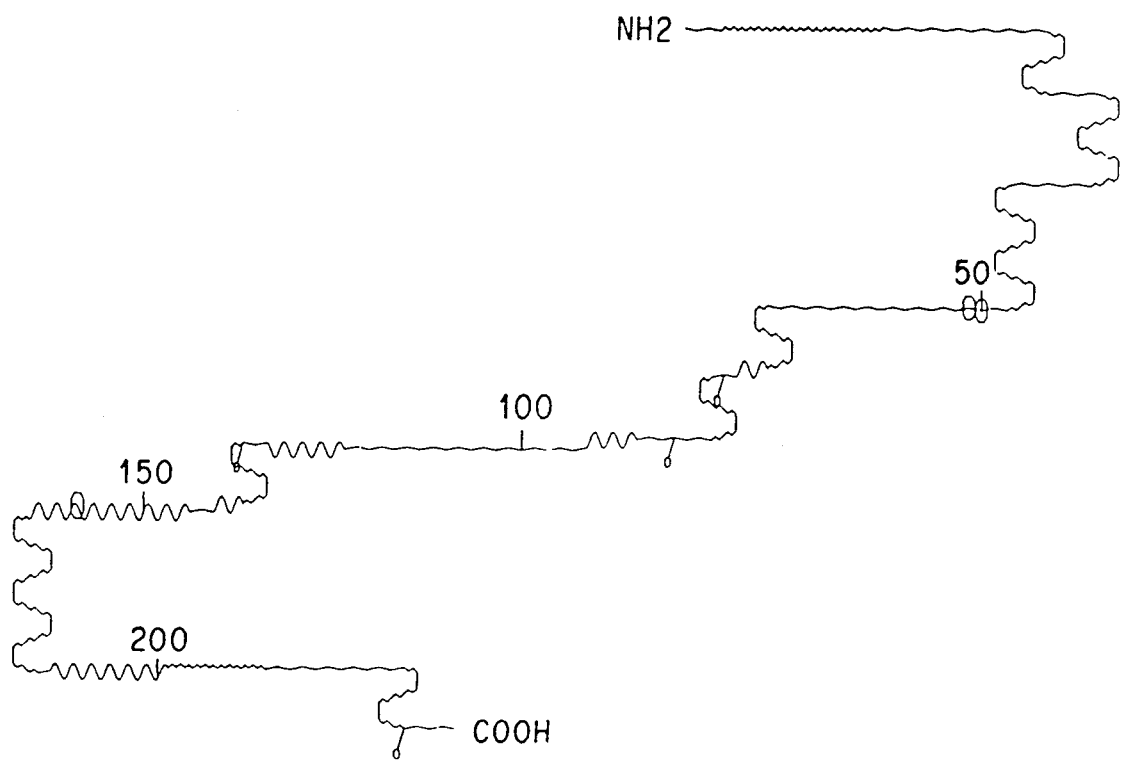
FIG. 10 shows a plotstructure representing a Chou-Fasman surface prediction analysis of the 30 kDa Bb polypeptide. Oblongated circles represent a predicted surface probability of $\geq 5.0$.

Reactive epitopes of the 30 kDa antigen may be identified by testing peptide fragments generated from isolated 30 kDa protein or, alternatively, by Kyte-Doolittle analysis of the amino acids of the protein. Hydrophilicity values of ≧1.0 were between amino acid segments 22–54, 67–87, 111–115, 128–134, 153–178, 184–186 and 209–226. Using Jameson-Wolf antigenicity and Kyte-Doolittle (1982) analysis to predict antigenic regions indicated regions 23–54, 64–87, 106–114, 128–133, 152–188 and 208–226. Hydrophilicity analysis was used to identify hydrophilic regions of the 30 kDa protein, Hopp, et al., (1981). A schematic representation of hydrophobic and hydrophilic regions of the protein is shown in FIG. 8. Corresponding regions of exposed surface groups are shown in FIG. 10. Predictions of antigenicity based on these data are shown schematically in FIG. 9 for the entire 30 kDa amino acid sequence.

EXAMPLE 10

The complete sequence of the DNA encoding the Virulence associated 30 kDa protein in Bb infections has been determined. Thus primers to this DNA segment are readily developed and PCR methods may be utilized to amplify the 30K DNA or segments of that DNA in biological samples, such as tissue, blood or serum. The following example illustrates a PCR technique contemplated as useful for the sensitive determination of the presence of 30K DNA in samples taken from infected individuals.

DETECTION OF *Bb* IN INDIVIDUALS SUSPECTED OF HAVING LYME DISEASE

Oligonucleotide primers are prepared from segments of sense or antisense strands of the DNA sequence of FIG. 2. The primers are synthesized by standard phosphoramidite chemistry. Concentrations of Taq DNA polymerase (Perkin Elmer/Cetus, Norwalk, Conn.), oligonucleotide primers, deoxyribonucleotides (Pharmacia, Piscataway, N.J.) and $Mg^{2+}$as well as amplification cycle lengths, numbers and temperatures are optimized.

All amplification reactions are performed in final volumes of 100 μl. A typical reaction may contain 50 mM KCL, 10 mM Tris-HCl, 3 mM $MgCl_2$, pH 8.3, 100 μ/ml gelatin, 70 picomoles of primers, 300 μM deoxyribonucleotides, 2.5 U of Taq polymerase and a sample of biological fluid suspected of containing *Bb* and which has been treated to assure access of primers to the target DNA (cell lysis, for example). Reactions are performed for 40 cycles in a Thermocycler (Perkin Elmer/Cetus) using the following: (1) denaturation for 1 min 15 sec at 94° C., (2) annealing for 1 min 15 sec at 60° C., and (3) extension for 1 min at 72° C. for an additional 10 min and then stored until analysis. To prevent false-positives due to contamination, all specimens are prepared under a laminar flow hood in a PCR dedicated facility remote from the principal laboratory.

Samples are analyzed by removing one tenth of the reaction volume (1μl) and electrophoresing through a 1% agarose gel containing 0.089 M Tris-HCl, 0.089 M borate, 0.002 M EDTA (THE) buffer and staining with 0.25 μg/ml ethidium bromide. Gels are photographed under ultraviolet light and, in some cases, transferred to 0.2 μm pore size nitrocellulose for Southern blot analysis. Other specimens may be applied directly to nitrocellulose using a Minifold I apparatus for dot blot DNA-DNA hybridization.

DNA probes for hybridizations are prepared from any of numerous selected DNA segments from the DNA shown in FIG. 2. The probe is radiolabeled with [α-$^{32}$P]dCTP using random hexanucleotide labeling. Southern and dot blot hybridizations are performed overnight at 65° C. in 1 M NaCl, 10% dextran sulfate, 1% SDS, 100 ug/ml sheared salmon sperm DNA and with $1\times10^8$ cpm/ml of labeled probe. After hybridization, blots are washed three times at 22° C. in 2 x SSC/0.1% SDS followed by two similar washes at 65° C. Autoradiography is performed at −70° C. on x-ray film for one to 24 hrs depending on the specific activity of the probe.

The present invention has been described in terms of particular embodiments found by the inventors to comprise preferred modes of practice of the invention. It will be appreciated by those of skill in the art that in light of the present disclosure numerous modifications and changes can be made in the particular embodiments exemplified without departing from the intended scope of the invention. All such modifications are intended to be included within the scope of the claims.

REFERENCES

The references listed below are incorporated herein by reference to the extent that they supplement, explain, provide a background for or teach methodology, techniques and/or compositions employed herein.

Adelman et al., DNA, 2, 183 (1983).

Anderson, J. F., Magnarelli, L. A., and McAninch, J. B., J. Clin. Microbiol. 26, 2209-2212 (1988).

Arimitsu, Y., Takashima, I., Yoshii, Z., Higashi, Y., Kameyama, S., and Mizuguchi, J., J. Infect. Dis., 163, 682-683 (1991).

Barbour, A. G., Yale J. Biol. Med. 57, 521-525 (1984).

Barbour, A. G., J. Clin. Microbiol. 26, 475-478 (1988).

Barthold, S. W., Beck, D. S., Hansen, G. M., Terwilliger, G. A., and Moody, K. D., J. Infect. Dis. 162, 133-138 (1990).

Beaucage, S. L., Caruthers, M. M. et al., Tet. Lett. 22, 1859-1862 (1981).

Bergström, S., Bundoc, V. G., and Barbour, A. G., Molec. Microbiol. 3, 479-486 (1989).

Bolivar et al., Gene, 2, 95 (1977).

Burman et al., *Mol. Mirobiol.* 4, 1715-26 (1990).

Centers Dis. Control, Lyme disease—Connecticut, Morbid. Mortal. Weekly Rep. 37 (1), 1-3 (1988).

Centers for Disease Control, Lyme disease--United States, 1987 and 1988, Morbid. Mortal. Weekly Rep. 38 (39), 668-672 (1989).

Chang et al., Nature 375, 615 (1978).

Craft, J. E., Grodzicki, R. L., and Steere, A. C., J. Infect. Dis. 149, 789-795 (1984).

Crea et al. 1978, Proc. Natl. Acad. Sci. U.S.A., 75:5765.

Eichenlaub, R., J. Bacteriol., 138, 559-566 (1979).

Fiers et al. (1978) Nature 273:113.

Fikrig, E., Barthold, S. W., Kantor, F. S., and Flavell, R. A., Science 250, 553-556 (1990).

Garnier, J., Osguthorpe, D. J. and Robson, B., J. Mol. Biol., 120, 97-120 (1978).

Goding, J. W., J. of Immunol. Methods, 39, 285-308 (1980).

Goeddel et al., Nucleic Acids Res. 8, 4057 (1980).

Goeddel et al. 1979, Nature, 281:544.

Goodman, J. L., Jarkovich, P., Kramber, J. M. and Johnson, R. C., Infect. Immun. 59, 269-278 (1991).

Hess et al. (1968) J. Adv. Enzyme Reg. 7:149.

Hinnebusch, J., Bergström, S., and Barbour, A. G., Molec. Microbiol., 4, 811-820 (1990).

Hitzeman et al., J. Biol. Chem. 255, 2073 (1980).

Holland et al. (1978) Biochemistry 17:4900.

Hopp, T. P. and Woods, K. R., Proc. Natl.. Acad. Sci. USA 78, 3824-3828 (1981).

Itakura et al., Science 198, 1056 (1977).

Johnson, R. C., and Kodner, C. B., Abstr. Gen. Mtg. Amer. Soc. Microbiol., Dallas, E-35, p. 123 (1991).

Jones, Genetics 84, 12 (1977).

Kingsman et al., Gene, 7, 141 (1979).

Kurtii, T. J., Munderloh, U. G., Johnson, R. C., and Ahlstrand, G. G., J. Clin. Microbiol. 25, 2054-2058 (1987).

Kyte, J. and Doolittle, R. F., J. Mol. Biol., 157, 105-132 (1982).

Lebech, A.-M., Hindersson, P., Vuust, J. and Hansen, K., J. Clin. Microbiol. 29, 731-737 (1991).

Magnarelli, L. A., Meegan, J. M., Anderson, J. F., and Chappell, W. A., J. Clin. Microbiol. 20, 181-184 (1984).

Magnarelli, L. A., Anderson, J. F., and Barbour, A. G. J. Infect. Dis. 159, 43-49 (1989).

Matsudaira, P., J. Biol. Chem. 262, 10035-10038 (1987).

Messing et al. 1981, Third Cleveland Symposium on Macromolecules and Recombinant DNA, Editor A. Walton, Elsevier, Amsterdam.

Moody, K. D., Barthold, S., and Tergwilliger, G. A., (1990), "Lyme borreliosis in laboratory animals, effect of host species and in vitro passage of *Borrelia burgdorferi.*"

Norris, S. J., Charon, N. W., Cook, R. G., Fuentes, M. D., and Limberger, R. J., J. Bacteriol. 170, 4072-4082 (1988).

O'Farrell, P. Z., Goodman, H. M., and O'Farrell, P. H., Cell 12 1133-1142 (1977).

Rahn, D. W. and Malawista, S. E., Annals Int. Med. 114, 472-481 (1991).

Rosa, P. A. and Schwan, T. G., J. Infect. Dis. 160, 1018-1029 (1989).

Sadziene, A., Thomas, D. D., Bundoc, V. G., Holt, S. C., and Barbour, A. G., J. Clin. Inv., in press (1991).

Schmid, G. P., Rev. Infect. Dis. 7, 41-49 (1985).

Shanafelt, M.-C., Hindersson, P., Soderberg, C., Mensi, N., Turck, C. W., Webb, D., Yssel, H. and Peltz, G., J. Immunol., 146, 3985-3992 (1991).

Siebwenlist et al., Cell 20, 269 (1980).

Steere, A. C., Malawista, S. E., Syndman, D. R. et al., Arthritis Rheum. 20, 7-17 (1977).

Steere, A. C., Taylor, E., Wilson, M. L., Levine, J. F. and Spielman, A., J. Infect. Dis. 154, 295-300 (1986).

Steere, A. C., Grodzicki, R. L., Kornblatt, A. N., et al., New Engl. J. Med. 308, 733-740 (1983).

Stinchcomb et al., Nature 282, 39 (1979).

Tissue Culture (1973) Academic Press. (eds.) Kruse and Patterson.

Tschemper et al., Gene, *Bb,* 157 (1980).

Wallich, R., Moter, S. E., Simon, M. M., Ebnet, K., Heiberger, A. and Kramer, M. D., Infect. Immun., 58, 1711-1719 (1990).

---

What is claimed is:

1. A DNA segment which comprises at least a 20 base pair segment according to SEQ ID NO:1 and which will bind to the complement of said sequence under high stringency conditions.

2. The DNA segment of claim 1 which comprises at least a 30 base pair segment corresponding to the DNA segment defined by SEQ ID NO:1.

3. The DNA segment of claim 1 which comprises at least a 40 base pair segment corresponding to the DNA segment defined by SEQ ID NO: 1.

4. The DNA segment of claim 1 which corresponds to the DNA sequence of SEQ ID NO:1.

5. The DNA segment of claim 1 wherein the DNA segment encodes an amino acid sequence comprising the sequencing from the amino acid Asp at position 23 through the amino acid Gln at position 54 according to SEQ ID NO:2.

6. The DNA segment of claim 1 wherein the DNA segment encodes an amino acid sequence comprising the sequence from the amino acid Leu at position 64 through the amino acid Ala at position 87 according to SEQ ID NO:2.

7. The DNA segment of claim 1 wherein the DNA segment encodes an amino acid sequence comprising the sequence from the amino acid Asp at position 106 through the amino acid Asn at position 114 according to SEQ ID NO:2.

8. The DNA segment of claim 1 wherein the DNA segment encodes an amino acid sequence comprising the sequence from the amino acid Lys at position 128 through the amino acid Ser at position 133 according to SEQ ID NO:2.

9. The DNA segment of claim 1 wherein the DNA segment encodes an amino acid sequence comprising the sequence from the amino acid Ala at position 152 through the amino acid Ala at position 188 according to SEQ ID NO:2.

10. The DNA segment of claim 1 wherein the DNA segment encodes an amino acid sequence comprising the sequence from the amino acid Asn at position 208 through the amino acid Lys at position 226 according to SEQ ID NO: 2.

11. A recombinant vector comprising the DNA segment of any one of claims 1, 3-4 or 6.

12. The recombinant vector of claim 11 wherein the DNA segment encodes an antigenic protein expressed in a low-passage, virulent strain of *B. burgdorferi*.

13. A recombinant cell comprising an extrachromosomal DNA segment in accordance with ATCC deposited plasmid accession number 75304 or ATCC accession number 75305.

14. The recombinant cell of claim 13 wherein the extrachromosomal DNA expresses a polypeptide encoded by the DNA of any of claims 1, 3 or 4.

15. A recombinant cell which is transformed with plasmic ATCC Accession No. 75304 and plasmid ATCC Accession No. 75305.

16. The recombinant cell of claim 15 wherein the cell is *B. burgdorferi* or *E. coli*.

17. A method of preparing transformed bacterial host cells, comprising the steps:
selecting a suitable bacterial host cells;
preparing a vector or plasmid containing the DNA segment of any of claims 1, 3-4 or 6; and
transforming the selected bacterial host cell.

18. The method of claim 17 wherein the plasmid or vector is capable of transforming the selected bacterial host cell to express a *B. burgdorferi* polypeptide encoded by the DNA of any of claims 1, 3-4 or 6.

19. The method of claim 18 wherein the expressed polypeptide is encoded by the DNA in accordance with any of claims 1, 3-4 or 6.

20. A *B. burgdorferi* transformant prepared by the method of claim 17.

21. A set of primers capable of priming amplification of the DNA according to SEQ ID NO:1.

22. A kit for the detection of *Borrelia burgdorferi* nucleic acids in a sample, the kit comprising a nucleic acid probe specific for the 30 kDa gene, together with means for detecting a specific hydridization between said probe and *Bb* nucleic acid.

* * * * *

UNITED STATES PATENT AND TRADEMARK OFFICE
CERTIFICATE OF CORRECTION

PATENT NO. : 5,246,844
DATED : September 21, 1993
INVENTOR(S) : Steven J. Norris, et al.

It is certified that error appears in the above-indentified patent and that said Letters Patent is hereby corrected as shown below:

On the title page, item (75) Inventors change "alan g. to read --Alan G.--.

Column 33, claim 5, line 5, change Sequencing to --sequence--.

Column 33, claim 11, line 37, delete 1, 3-4 or 6; insert 1-4

Column 34, claim 14, delete 1, 3 or 4; insert 1-4

Column 34, claim 17, delete 1, 3-4 or 6; insert 1-4

Column 34, claim 17, line 18, change cells to --cell--.

Column 34, claim 18, delete 1, 3-4 or 6; insert 1-4

Column 34, claim 19, delete 1, 3-4 or 6: insert 1-4

Signed and Sealed this

Fifth Day of April, 1994

Attest:

BRUCE LEHMAN

Attesting Officer          Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1079 base pairs
        ( B ) TYPE: nucleic acid
        ( C ) STRANDEDNESS: unknown
        ( D ) TOPOLOGY: linear ( x i ) SEQUENCE DESCRIPTION: SEQ ID NO:1:

```
TTTTTTTGCT  TGTTTTTAGC  ATCATTAAAC  ATCCTTTCAA  TACTCACTAT  TGTTTTCTTA      60
GCCTTAAGCT  AGCCAAGCTA  AATAGAAATT  AGTAGGCAAT  TGATATTAAA  ATATAATTGA     120
TATTAAAATA  TAATTGATAT  TAAAATATAA  TTGATATTAA  AATATAATTG  ATATTAAAAT     180
ATAATTGATA  TTGAAATATA  ATTGATATTA  AAATATAATT  TAAGACATTA  TATTTAAGGA     240
GTATAAATAT  GAAAAAATTA  ATAAAAATAC  TACTGTTAAG  TTTATTTTTA  TTGCTCTCAA     300
TATCTTGTGT  TCATGATAAA  CAAGAATTAT  CATCAAAATC  TAATTTAAAT  AATCAAAAAG     360
GATATTTAGA  TAATGAAGGC  GCAAATTCAA  ATTACGAATC  AAAAAAACAG  AGCATATTAA     420
GTGAGTTAAA  TCAGTTATTA  AAGCAAACTA  CAAATTCACT  AAAAGAAGCC  AAAAATACAA     480
CAGATAATTT  AAATGCATCA  AATGAGGCAA  ATAAAGTTGT  AGAAGCGGTT  ATAAATGCAG     540
TTAATTTAAT  TTCATCTGCT  GCAGATCAAG  TAAAAAGTGC  AACAAAAAAT  ATGCATGATT     600
TAGCTCAAAT  GGCAGAAATA  GATTTAGAAA  AAATAAAGAA  CTCTAGTGAT  AAAGCAATAT     660
TTGCATCTAA  TCTTGCAAAA  GAAGCATATA  GCCTTACTAA  AGCAGCAGAA  CAAAACATGC     720
AAAAACTGTA  TAAAGAGCAA  CAAAAAATAT  CAGAATCAGA  ATCAGAATCT  GACTATTCTG     780
```

-continued

```
ATTCTGCTGA AATAAAACAA GCTAAAGAGG CCGTAGAAAT AGCTTGGAAA GCTACAGTAG      840

AAGCAAAAGA TAAGTTAATT GATGTAGAAA ATACAGTCAA AGAGACATTG GATAAAATAA      900

AGACAGAAAC TACGAACAAT ACAAAGCTTG CAGATATAAA AGAAGCAGCA GAGTTAGTAT      960

TACAAATAGC TAAGAATGCA AAGGAAATAG TACAAGAAGT TGTGGCCTTG TTAAATACTT     1020

AAATAAATAA AAGATGGAAG TAAGGAAGGA AGAATAATTT TGTGCTGGCT TATCCTTCC      1079
```

(2) INFORMATION FOR SEQ ID NO:2:

(i) SEQUENCE CHARACTERISTICS:
        (A) LENGTH: 257 amino acids
        (B) TYPE: amino acid
        (D) TOPOLOGY: linear (ii) MOLECULE TYPE: peptide (xi) SEQUENCE DESCRIPTION: SEQ ID NO:2:

```
Met Lys Lys Leu Ile Lys Ile Leu Leu Leu Ser Leu Phe Leu Leu Leu
 1               5                  10                  15

Ser Ile Ser Cys Val His Asp Lys Gln Glu Leu Ser Ser Lys Ser Asn
                20                  25                  30

Leu Asn Asn Gln Lys Gly Tyr Leu Asp Asn Glu Gly Ala Asn Ser Asn
            35                  40                  45

Tyr Glu Ser Lys Lys Gln Ser Ile Leu Ser Glu Leu Asn Gln Leu Leu
 50                  55                  60

Lys Gln Thr Thr Asn Ser Leu Lys Glu Ala Lys Asn Thr Thr Asp Asn
 65                  70                  75                  80

Leu Asn Ala Ser Asn Glu Ala Asn Lys Val Val Glu Ala Val Ile Asn
                85                  90                  95

Ala Val Asn Leu Ile Ser Ser Ala Ala Asp Gln Val Lys Ser Ala Thr
            100                 105                 110

Lys Asn Met His Asp Leu Ala Gln Met Ala Glu Ile Asp Leu Glu Lys
            115                 120                 125

Ile Lys Asn Ser Ser Asp Lys Ala Ile Phe Ala Ser Asn Leu Ala Lys
    130                 135                 140

Glu Ala Tyr Ser Leu Thr Lys Ala Ala Glu Gln Asn Met Gln Lys Leu
145                 150                 155                 160

Tyr Lys Glu Gln Gln Lys Ile Ser Glu Ser Glu Ser Glu Ser Asp Tyr
                165                 170                 175

Ser Asp Ser Ala Glu Ile Lys Gln Ala Lys Glu Ala Val Glu Ile Ala
            180                 185                 190

Trp Lys Ala Thr Val Glu Ala Lys Asp Lys Leu Ile Asp Val Glu Asn
        195                 200                 205

Thr Val Lys Glu Thr Leu Asp Lys Ile Lys Thr Glu Thr Thr Asn Asn
210                 215                 220

Thr Lys Leu Ala Asp Ile Lys Glu Ala Ala Glu Leu Val Leu Gln Ile
225                 230                 235                 240

Ala Lys Asn Ala Lys Glu Ile Val Gln Glu Val Val Ala Leu Leu Asn
                245                 250                 255

Thr
```